United States Patent
Hazani

(10) Patent No.: US 10,052,443 B2
(45) Date of Patent: Aug. 21, 2018

(54) NEBULIZERS AND USES THEREOF

(71) Applicant: OMEGA LIFE SCIENCE LTD., Migdal Haemek (IL)

(72) Inventor: Miron Hazani, Haifa (IL)

(73) Assignee: OMEGA LIFE SCIENCE LTD., Migdal Haemek (IL)

( * ) Notice: Subject to any disclaimer, the term of this patent is extended or adjusted under 35 U.S.C. 154(b) by 0 days.

(21) Appl. No.: 15/516,907

(22) PCT Filed: Oct. 12, 2015

(86) PCT No.: PCT/IL2015/051015
§ 371 (c)(1),
(2) Date: Apr. 5, 2017

(87) PCT Pub. No.: WO2016/059630
PCT Pub. Date: Apr. 21, 2016

(65) Prior Publication Data
US 2017/0304561 A1   Oct. 26, 2017

Related U.S. Application Data

(60) Provisional application No. 62/062,966, filed on Oct. 13, 2014, provisional application No. 62/066,401, (Continued)

(51) Int. Cl.
*A61M 11/02* (2006.01)
*A61M 11/00* (2006.01)
*A61M 15/00* (2006.01)

(52) U.S. Cl.
CPC ........... *A61M 11/02* (2013.01); *A61M 11/003* (2014.02); *A61M 11/005* (2013.01);
(Continued)

(58) Field of Classification Search
CPC ........ A61M 11/005; A61M 2205/0288; A61M 2205/103; A61M 2205/12;
(Continued)

(56) References Cited

U.S. PATENT DOCUMENTS

| | | |
|---|---|---|
| 1,023,063 A | 4/1912 | Bassford |
| 1,132,679 A | 3/1915 | Murray |

(Continued)

FOREIGN PATENT DOCUMENTS

| | | |
|---|---|---|
| DE | 1817899 | 7/1973 |
| EP | 0135390 | 3/1985 |

(Continued)

OTHER PUBLICATIONS

Atkinson et al., (2009) Natural ventilation for infection control in health-care settings. World Health Organization.
(Continued)

*Primary Examiner* — Gregory Anderson
*Assistant Examiner* — Jonathan Paciorek
(74) *Attorney, Agent, or Firm* — The Roy Gross Law Firm, LLC; Roy Gross

(57) ABSTRACT

The present disclosure generally relates to the field of nebulizers for aerosol generation and methods of using same for treating diseases and disorders.

**20 Claims, 19

Related U.S. Application Data filed on Oct. 21, 2014, provisional application No. 62/180,627, filed on Jun. 17, 2015.

(52) U.S. Cl.
CPC . *A61M 15/0001* (2014.02); *A61M 2205/0288* (2013.01); *A61M 2205/103* (2013.01); *A61M 2205/12* (2013.01); *A61M 2205/3331* (2013.01)

(58) Field of Classification Search
CPC .......... A61M 2205/3331; A61M 11/02; A61M 11/003; A61M 15/0001
See application file for complete search history.

(56) References Cited

U.S. PATENT DOCUMENTS

| | | |
|---|---|---|
| 2,276,878 A | 3/1942 | Rose |
| 2,284,591 A | 5/1942 | Rose |
| 3,570,038 A | 3/1971 | Jones |
| 3,583,635 A | 6/1971 | Lemelson |
| 3,762,409 A | 10/1973 | Lester |
| 3,812,854 A | 5/1974 | Buckles |
| RE30,046 E | 7/1979 | van Amerongen |
| 4,743,407 A | 5/1988 | Apel |
| 4,757,812 A | 7/1988 | Arborelius, Jr. |
| 4,832,012 A * | 5/1989 | Raabe .................. A61M 16/16 128/200.17 |
| 4,907,581 A | 3/1990 | King |
| 4,941,618 A | 7/1990 | Hildebrand |
| 5,030,390 A | 7/1991 | Nicholls |
| 5,048,729 A | 9/1991 | Pritchard |
| 5,261,601 A | 11/1993 | Ross |
| 5,277,175 A | 1/1994 | Riggs |
| 5,301,664 A | 4/1994 | Sievers |
| 5,379,760 A | 1/1995 | Ryder |
| 5,431,345 A | 7/1995 | Lund |
| 5,479,920 A | 1/1996 | Piper |
| 5,497,763 A | 3/1996 | Lloyd |
| 5,535,989 A | 7/1996 | Sen |
| 5,544,646 A | 8/1996 | Lloyd |
| 5,570,682 A | 11/1996 | Johnson |
| 5,603,314 A | 2/1997 | Bono |
| 5,685,291 A | 11/1997 | Marsh |
| 5,718,222 A | 2/1998 | Lloyd |
| 5,724,959 A | 3/1998 | McAughey |
| 5,755,221 A | 5/1998 | Bisgaard |
| 5,810,755 A | 9/1998 | Leveen |
| 5,823,179 A | 10/1998 | Grychowski |
| 5,833,057 A | 11/1998 | Char |
| 5,855,564 A | 1/1999 | Ruskewicz |
| 5,858,313 A | 1/1999 | Park |
| 5,915,378 A | 6/1999 | Lloyd |
| 6,062,212 A | 5/2000 | Davison |
| 6,070,575 A | 6/2000 | Gonda |
| 6,168,140 B1 | 1/2001 | Akazawa |
| 6,230,706 B1 | 5/2001 | Gonda |
| 6,315,272 B1 | 11/2001 | Stanek |
| 6,467,477 B1 | 10/2002 | Frank |
| D471,626 S | 3/2003 | Terada |
| 6,527,257 B1 | 3/2003 | Schuld |
| 6,530,370 B1 | 3/2003 | Heinonen |
| 6,598,602 B1 | 7/2003 | Sjoeholm |
| 6,606,989 B1 | 8/2003 | Brand |
| 6,647,987 B2 | 11/2003 | Gonda |
| 7,013,894 B2 | 3/2006 | McFarland |
| 7,163,014 B2 | 1/2007 | Nichols |
| 7,246,617 B1 | 7/2007 | Harmer |
| 7,373,938 B2 | 5/2008 | Nichols |
| 7,562,656 B2 | 7/2009 | Gallem |
| 7,748,382 B2 | 7/2010 | Denyer |
| 7,900,627 B2 | 3/2011 | Aylsworth |
| 7,984,710 B2 | 7/2011 | Von Schuckmann |
| 8,261,738 B2 | 9/2012 | Denyer |
| 8,371,299 B2 | 2/2013 | Denyer |
| 8,464,706 B2 | 6/2013 | Crockford |
| 8,491,491 B2 | 7/2013 | Haefner |
| 8,607,786 B2 | 12/2013 | Denyer |
| 8,820,316 B2 | 9/2014 | Crockford |
| 8,960,189 B2 | 2/2015 | Morrison |
| 9,050,424 B2 | 6/2015 | Van Der Mark |
| 9,050,425 B2 | 6/2015 | Van Der Mark |
| 9,060,715 B2 | 6/2015 | Schipper |
| 9,132,244 B2 | 9/2015 | Dyche |
| 9,135,397 B2 | 9/2015 | Denyer |
| 9,352,107 B2 | 5/2016 | Von Hollen |
| 9,494,506 B2 | 11/2016 | Dyche |
| 9,572,944 B2 | 2/2017 | Van Der Sluis |
| 9,586,223 B2 | 3/2017 | Bentvelsen |
| 2002/0073991 A1 | 6/2002 | Gonda |
| 2004/0045546 A1 | 3/2004 | Hirsh |
| 2004/0113292 A1 | 6/2004 | Sadykhov |
| 2004/0123863 A1 | 7/2004 | Wang |
| 2005/0039744 A1 | 2/2005 | Szirmai |
| 2005/0066968 A1 * | 3/2005 | Shofner ................. A61B 5/411 128/204.18 |
| 2007/0003603 A1 | 1/2007 | Karandikar |
| 2007/0175476 A1 | 8/2007 | Lipowicz |
| 2008/0082139 A1 | 4/2008 | Means |
| 2010/0031964 A1 | 2/2010 | Turek |
| 2010/0078015 A1 | 4/2010 | Imran |
| 2010/0092746 A1 | 4/2010 | Coant |
| 2010/0192321 A1 | 8/2010 | Tuman |
| 2012/0318259 A1 | 12/2012 | Sadykhov |
| 2013/0228169 A1 | 9/2013 | Stangl |

FOREIGN PATENT DOCUMENTS

| | | |
|---|---|---|
| EP | 2149359 | 2/2010 |
| GB | 322927 | 12/1929 |
| GB | 2404867 A | 2/2005 |
| JP | H06345194 | 12/1994 |
| WO | 0050111 | 8/2000 |
| WO | 0058022 | 10/2000 |
| WO | 0166064 | 9/2001 |
| WO | 2005102428 | 11/2005 |
| WO | 2008048234 | 4/2008 |
| WO | 2010104018 A1 | 9/2010 |

OTHER PUBLICATIONS

"Flat". Merriam-Webster.com. Retrieved Sep. 19, 2016, from http://www.meriam-webster.com/dictionary/flat.
"Metallic". Oxforddictionaries.com. Retrieved Sep. 19, 2016, from https://en.oxforddictionaries.com/definition/metallic.
Zadorecki & Flodin, (1985) Surface modification of cellulose fibers. II. The effect of cellulose fiber treatment on the performance of cellulose-polyester composites. Journal of applied polymer science, 30(10), 3971-3983.

* cited by examiner

NEBULIZERS AND USES THEREOF

RELATED APPLICATION DATA

This application is the U.S. National Stage of International Application No. PCT/IL2015/051015 filed Oct. 12, 2015, which claims the benefit of U.S. Provisional Patent Application No. 62/062,966 filed Oct. 13, 2014. Each of the foregoing applications is hereby incorporated by reference in its entirety for all purposes.

TECHNICAL FIELD

The present disclosure generally relates to the field of nebulizers for aerosol generation and methods of using same for treating diseases and disorders.

BACKGROUND

Nebulizers are commonly used for delivering aerosol medication to patients via the respiratory system. Desirably, for efficient delivery of medication, the droplet diameter of the aerosol should be sufficiently small so as to reach the lungs of the patient without being obstructed by objects or organs (such as, the inner surface of the nozzle in the nebulizer and the mouth cavity perimeters) and large enough so as to remain in the lungs during exhalation.

The main techniques for producing aerosol in nebulizers include vibrating Mesh technology, jet nebulizers and ultrasonic wave nebulizers. Common to these techniques is the challenge to deliver large volume of medication to the patient while keeping the diameter of the droplets within desired limits.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

According to some embodiments, there are provided herein devices, systems and methods for generating aerosol for medication delivery using a porous medium and a displaceable spreading mechanism or liquid absorbing material. The aerosol may be generated by wetting the porous medium. Wetting may include applying the displaceable spreading mechanism thereby spreading liquid on the surface of the porous medium. Alternatively, wetting may include wetting the liquid absorbing material, then pressing it against the porous medium, or a surface thereof, resulting in a relatively uniform wetting of the porous medium. Once the porous medium, or a surface thereof, is wet, applying pressure gradient upon the porous medium results in the generation of aerosol.

According to some embodiments, applying pressure gradient entails introducing pressurized air to one side of the porous medium. According to some embodiments, applying pressure gradient entails introducing vacuum or sub-atmospheric pressure near one side of the porous medium. According to some embodiments, applying pressure gradient upon the porous medium entails having different pressure levels between two sides or surfaces of the porous medium.

Advantageously, the devices, systems and methods disclosed herein provide a relatively uniform or homogeneous wetting of the porous surface that may result in small diameter aerosol droplets, and confer the ability to yield such small diameter aerosol drops with high efficiency.

According to some embodiments, there is provided a nebulizer comprising a porous medium configured to produce aerosols, a displaceable wetting mechanism configured to spread a liquid over the porous medium thereby to wet the porous medium and a gas channel configured to introduce pressure gradient to the porous medium.

According to some embodiments, the displaceable wetting mechanism may include a rotatable elongated member.

According to some embodiments, the rotatable elongated member is configured to move across the surface of the porous medium, thereby to homogeneously or semi-homogeneously spread the liquid on the surface.

According to some embodiments, the elongated member is axially movable. According to some embodiments, the elongated member is movable to cover approximately all the surface of the porous medium.

The term "approximately" as used herein may refer to the percentage of surface of the porous medium that may be coated with liquid by the spreading movement of the elongated member. Approximately may refer to more than 50% coverage, more than 60% coverage, at least 70% coverage, at least 80% coverage, at least 90% coverage or at least 95% coverage. According to some embodiments, the wetting mechanism further includes an actuator, configured to displace or induce the displacement of the elongated member.

The term "displacement" as used herein may be interchangeable with any one or more of the terms movement, movement across. This term may refer to the motion of the wetting mechanism across, or along, at least one surface of the porous medium.

According to some embodiments, the elongated member comprises a first magnet, and the actuator comprises a second magnet, magnetically associated with the first magnet of the elongated member, such that by moving/displacing the second magnet of the actuator, a displacing of the elongated member is induced.

According to some embodiments, said first magnet may comprise a plurality of magnets. According to some embodiments, said second magnet may comprise a plurality of magnets.

According to some embodiments, one or more of the plurality of magnets includes an electromagnet. According to some embodiments, the actuator comprises a motor configured to displace the elongated member.

According to some embodiments, the elongated member is at least partially covered with polytetrafluoroethylene (PTFE), commercially knowns as Teflon®, or any other appropriate coating materials.

According to some embodiments, the elongated member is an elongated tubular member. According to some embodiments, the elongated member is movable by an actuator, mechanically connected thereto. According to some embodiments, the elongated member is movable by the air-flow within the nebulizer and/or through the porous material.

According to some embodiments, the elongated member is a roller. According to some embodiments, the elongated member is a smearing device. According to some embodiments, the elongated member is a spreading device. According to some embodiments, the elongated member is configured to force at least portions of the liquid to at least some of the pores of the porous medium.

According to some embodiments, the nebulizer further comprises a spacer configured to elevate said displaceable wetting mechanism from the surface of said porous medium. According to some embodiments, said spacer is integrally formed with said displaceable wetting mechanism. According to some embodiments, said spacer comprises a protrusion in said displaceable wetting mechanism. According to some embodiments, said spacer is configured to be placed between said displaceable wetting mechanism and the surface of said porous medium. According to some embodiments, said pacer comprises a ring-shaped configured to facilitate low-friction displacement of said displaceable wetting mechanism.

According to some embodiments, the nebulizer further comprises a liquid deploying mechanism configured to controllably deploy a liquid on the surface of said porous medium for being spread by said displaceable wetting mechanism. According to some embodiments, said liquid deploying mechanism comprises a conduit. According to some embodiments, said conduit has a receiving end, configured to obtain a liquid from a liquid source, and a deploying end, configured to deploy the liquid on the surface of said porous medium. According to some embodiments, said deploying end of said conduit is flexible and configured to flexibly move by the displacement of said displaceable wetting mechanism, thereby deploy the liquid at more than one location on the surface of said porous medium.

According to some embodiments, the nebulizer further comprises an opening configured to deliver the aerosols to a respiratory system of a subject.

According to some embodiments, there is provided a nebulizer comprising a porous medium configured to produce aerosols, a liquid absorbing material configured to absorb a liquid, a wetting mechanism configured to press the liquid absorbing material against the porous medium, thereby to wet the porous medium with the liquid absorbed in the liquid absorbing material and a gas channel configured to introduce pressure gradient to the porous medium.

According to some embodiments, the liquid absorbing material is a sponge, a tissue or foam.

According to some embodiments, the liquid absorbing material is configured to act as an impactor for aerosols produced by the porous medium.

According to some embodiments, the liquid absorbing material is configured to act as a filter for aerosols produced by the porous medium.

According to some embodiments, the liquid absorbing material comprises at least one pharmaceutical composition.

According to some embodiments, the nebulizer further comprises a first container, configured to contain liquids to be delivered to the liquid absorbing material.

According to some embodiments, the nebulizer further comprises a second container configured to contain at least one pharmaceutical composition. According to some embodiments, the liquids comprise water.

According to some embodiments, the gas channel is connected to a gas source.

According to some embodiments, there is provided a nebulizer cartridge, comprising a porous medium, and a displaceable wetting mechanism configured to spread a liquid over the porous medium, thereby to wet the porous medium.

According to some embodiments, the porous medium comprises a plurality of pores, wherein at least some of said plurality of pores comprise liquid. According to some embodiments, said liquid comprises a pharmaceutical composition.

According to some embodiments, the displaceable wetting mechanism further comprises an actuator configured to displace or induce the displacement of the rotatable elongated member. According to some embodiments, the rotatable elongated member comprises a first magnet, and the actuator comprises a second magnet, magnetically associated with said first magnet, such that by moving the second magnet displacement of the rotatable elongated member is induced. According to some embodiments, said first and/or second magnet comprises a plurality of magnets.

According to some embodiments, the cartridge is configured to be inserted to a nebulizer main body. According to some embodiments, the nebulizer main body comprises an opening configured to deliver aerosols.

According to some embodiments, the nebulizer main body further comprises a nozzle mechanically connected to the opening.

According to some embodiments, there is provided a nebulizer cartridge, comprising a porous medium and a liquid absorbing material, configured to be pressed against the porous medium, thereby produce aerosols.

According to some embodiments, the liquid absorbing material comprises a sponge.

According to some embodiments, the liquid absorbing material comprises a liquid absorbed therein.

According to some embodiments, the liquid is a pharmaceutical composition.

According to some embodiments, the pharmaceutical composition is for treating a disease via inhalation.

According to some embodiments, the cartridge further comprises a container, configured to contain liquid to be delivered to the liquid absorbing material.

According to some embodiments, the cartridge is configured to be inserted to a nebulizer main body. According to some embodiments, the nebulizer main body comprises an opening configured to deliver aerosols.

According to some embodiments, the nebulizer main body further comprises a nozzle mechanically connected to the opening.

According to some embodiments, the nebulizer further comprises a container, configured to contain liquid to be delivered to the liquid absorbing material.

According to some embodiments, the liquid comprises a pharmaceutical composition.

According to some embodiments, there is provided a nebulizer system comprising a housing, an opening in the housing configured to deliver aerosols to a subject, a cartridge, a receptacle configured to receive the cartridge and a gas channel, wherein the cartridge comprises a porous medium configured to produce aerosols and a wetting mechanism configured to spread the liquid absorbing material onto the porous medium.

According to some embodiments, the nebulizer system further comprises a nozzle, mechanically connected to the opening.

According to some embodiments, the wetting mechanism comprises a rotatable elongated member. According to some embodiments, the rotatable elongated member comprises an actuator configured to displace or induce the displacement of the rotatable elongated member.

According to some embodiments, the actuator comprises a shaft, configured to be mechanically connected to the wetting mechanism.

According to some embodiments, there is provided a nebulizer system comprising a housing, an opening in the housing configured to deliver aerosols to a subject, a cartridge, a receptacle configured to receive the cartridge and a gas channel, wherein the cartridge comprises a porous medium and a liquid absorbing material, configured to be pressed against the porous medium, thereby produce aerosols.

According to some embodiments, the liquid absorbing material comprises a sponge, a tissue or foam.

According to some embodiments, the liquid absorbing material comprises at least one pharmaceutical composition at least partially absorbed therein.

The term "partially absorbed therein" as used herein refers to the percentage of liquid absorbed in the pores of the porous material, wherein 0% refers to a porous material where all of its pores are vacant of liquid. Thus, the term "partially absorbed therein" may refer to a porous material wherein at least 0.005% of the pores contain liquid, or wherein the overall contents of the vacant space within the porous material occupied with liquid is 0.005%. According to some embodiments, partially absorbed therein refers to at least 0.001% liquid contents within the porous material. According to some embodiments, partially absorbed therein refers to at least 0.05% liquid contents within the porous material. According to some embodiments, partially absorbed therein refers to at least 0.01% liquid contents within the porous material. According to some embodiments, partially absorbed therein refers to at least 0.5% liquid contents within the porous material. According to some embodiments, partially absorbed therein refers to at least 0.1% liquid contents within the porous material. According to some embodiments, partially absorbed therein refers to at least 1% liquid contents within the porous material. According to some embodiments, partially absorbed therein refers to at least 5% liquid contents within the porous material. According to some embodiments, partially absorbed therein refers to at least 10% liquid contents within the porous material. According to some embodiments, partially absorbed therein refers to at least 20% liquid contents within the porous material. According to some embodiments, partially absorbed therein refers to at least 30% liquid contents within the porous material. According to some embodiments, partially absorbed therein refers to at least 40% liquid contents within the porous material. According to some embodiments, partially absorbed therein refers to at least 50% liquid contents within the porous material.

According to some embodiments, the term "partially absorbed therein" may refer to the content of liquid within the volume of pores located on the surface and in the immediate vicinity of the surface (sub surface) of a porous medium. According to some embodiments, the volume of the sub-surface may extend from the surface to a depth of about 50 micron from the surface.

According to some embodiments, partially absorbed therein refers to a porous material wherein at least 0.5% of the surface and sub-surface pores contain liquid. According to some embodiments, partially absorbed therein refers to at least 1% liquid contents within the surface and sub-surface pores. According to some embodiments, partially absorbed therein refers to at least 10% liquid contents within the surface and sub-surface pores. According to some embodiments, partially absorbed therein refers to at least 20% liquid contents within the surface and sub-surface pores. According to some embodiments, partially absorbed therein refers to at least 30% liquid contents within the surface and sub-surface pores. According to some embodiments, partially absorbed therein refers to at least 40% liquid contents within the surface and sub-surface pores. According to some embodiments, partially absorbed therein refers to at least 50% liquid contents within the surface and sub-surface pores. According to some embodiments, partially absorbed therein refers to at least 60% liquid contents within the surface and sub-surface pores.

According to some embodiments, the nebulizer system further comprises a first container, configured to contain liquids to be delivered to the liquid absorbing material.

According to some embodiments, the nebulizer system further comprises a second container configured to contain at least one pharmaceutical composition.

According to some embodiments, the gas channel is connected to a gas source.

According to some embodiments, there is provided a method for producing aerosols, the method comprises:

providing a nebulizer comprising a porous medium configured to produce aerosols, a displaceable wetting mechanism configured to spread the liquid over the porous medium thereby to wet the porous medium and a gas channel, wherein said porous medium is having two sides, a first side facing the displaceable wetting mechanism;

providing a liquid;

operating the displaceable wetting mechanism thereby spreading the liquid onto said first side of the porous medium; and connecting the gas channel to a pressure source and introducing pressure gradient to the porous medium thereby producing aerosol at the first side of the porous medium, the aerosol comprises droplets of the liquid;

According to some embodiments, there is provided a method for producing aerosols, the method comprises:

providing a nebulizer comprising a porous medium configured to produce aerosols, a liquid absorbing material configured to absorb a liquid, a wetting mechanism configured to press the liquid absorbing material against the porous medium, and a gas channel configured to introduce pressure gradient to the porous medium, wherein the porous medium is having two sides wherein a first side is facing the liquid absorbing material;

providing liquid;

wetting the liquid absorbing material with the liquid;

pressing the liquid absorbing material against the porous medium; and introducing pressure gradient to the porous medium thereby producing aerosol at the first side of the porous medium, the aerosol comprises droplets of the liquid.

According to some embodiments, the method further comprises delivering the aerosols to a respiratory system of a subject in need thereof.

According to some embodiments, the method further comprises providing a pharmaceutical composition and mixing the pharmaceutical composition with the liquid, prior to wetting the liquid absorbing agent.

According to some embodiments, the liquid absorbing material comprises a pharmaceutical composition.

According to some embodiments, the method further comprises iterating the following steps at least one more time: pressing the liquid absorbing material against the porous medium, introducing pressure gradient to the porous medium and producing aerosol at the first side of the porous medium, the aerosol comprises droplets of the liquid.

According to some embodiments, pressing comprises applying a pressing force that varies over iterations.

According to some embodiments, the method further comprises providing a cleansing liquid and iterating the following steps with the cleansing liquid: wetting the liquid absorbing material with the liquid, pressing the liquid absorbing material against the porous medium, introducing pressure gradient to the porous medium and producing aerosol at the first side of the porous medium, the aerosol comprises droplets of the liquid.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

There is provided, according to some embodiments, a nebulizer comprising a porous medium that is configured to produce aerosol, a liquid absorbing material configured to absorb a liquid, a wetting mechanism configured to press the liquid absorbing material against the porous medium or a first surface of the porous medium, thereby to wet the porous medium with the liquid absorbed in the liquid absorbing material and a gas channel configured to introduce pressure gradient to the porous medium.

The nebulizer disclosed herein may function as an inhaler under some circumstances. Thus, the terms 'nebulizer' and 'inhaler' as used herein may be interchangeable.

The terms 'medium' and 'material' as used herein are interchangeable.

Figure 1:
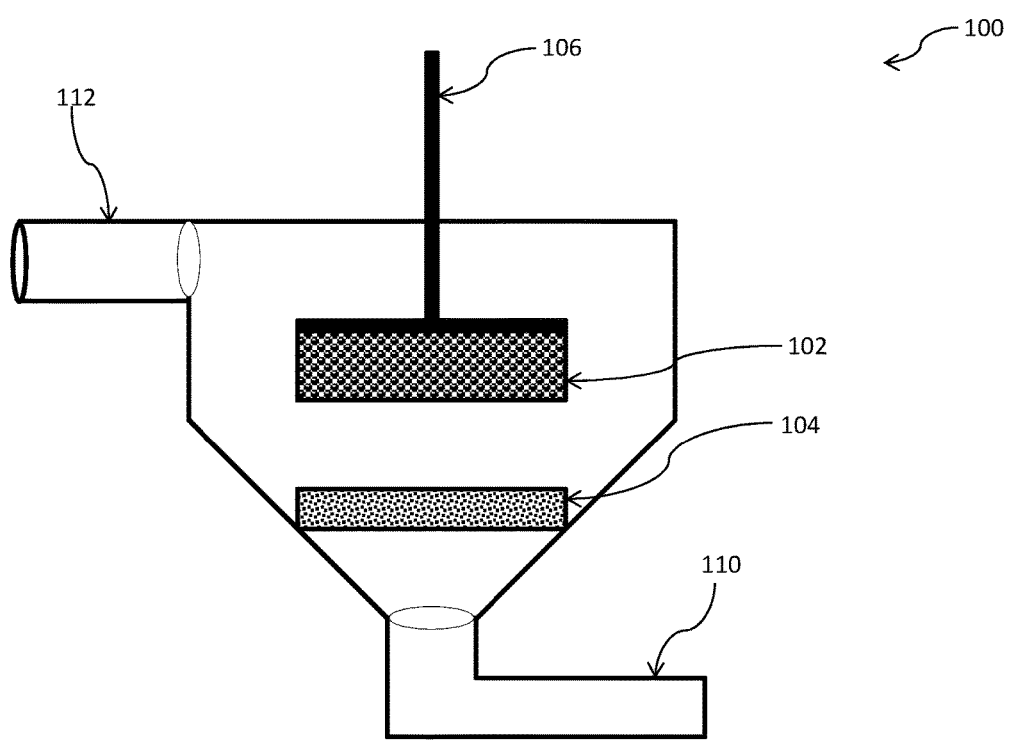
FIG. 1 schematically illustrates a nebulizer with a porous medium, according to some embodiments.

Reference is now made to FIG. 1, which schematically illustrates a nebulizer 100 comprising a porous medium 104, according to some embodiments. Nebulizer 100 further comprises a sponge 102, a wetting mechanism 106, a gas channel 110 and an outlet 112. Wetting mechanism 106 comprises a rod and a solid plate connected to sponge 102.

The terms 'nozzle' and 'outlet' as used herein are interchangeable.

In some embodiment, the liquid absorbing material is a sponge, a tissue, a foam material, a fabric or any other material capable of fully or partially retrievably absorbing liquids. Each possibility is a separate embodiment of the invention.

According to some embodiments, the liquid absorbing material is configured to enable small diameter droplets to pass through the structure thereof and to obstruct large diameter droplets from passing through the material thereof.

According to some embodiments, the liquid absorbing material is configured to filter the passage of droplets depending on their diameter, such that large diameter droplets are obstructed by the liquid absorbing material.

The terms 'sponge' and 'liquid absorbing material' as used herein refer to any material that is capable of incorporating, taking in, drawing in or soaking liquids, and upon applying physical pressure thereto, release a portion or the entire amount/volume of the absorbed liquid. The physical pressure may be achieved for example by pressing the material against a solid structure.

According to some embodiments, the liquid absorbing material is having two sides, wherein a first side is facing the wetting mechanism and a second side is facing the porous medium. According to some embodiments, the wetting mechanism is a movable solid medium facing the first side of the liquid absorbing material. According to some embodiments, the wetting mechanism is in close proximity to the first side of the liquid absorbing material. According to some embodiments, the wetting mechanism is attached to the first side of the liquid absorbing material.

The term 'attached to' as used herein includes, but is not limited to, linked, bonded, glued, fastened and the like.

According to some embodiments, the porous medium is having two sides, wherein a first side is facing the liquid absorbing material and a second side is facing the gas channel. According to some embodiments, the first side of the porous medium is facing the liquid absorbing material and the gas channel. According to some embodiments, the liquid absorbing material and the porous medium are in close proximity. According to some embodiments, the first side of the liquid absorbing material and the first side of the porous medium are in close proximity.

Without being bound by any theory or mechanism, a pressure gradient at the porous medium reflects the presence of value difference between the pressure at the first side of the porous material and the pressure at the second side of the porous material, such that pressure values vary inside the volume of the porous medium. These values range from the pressure value at the first side to the pressure value at the second side of the porous medium.

According to some embodiments, the gas channel is a gas delivery channel configured to introduce pressure gradient to the porous medium. According to some embodiments, the gas channel is a gas delivery channel configured to introduce pressurized gas to the porous medium. According to some embodiments, the gas channel is a gas suction channel configured to introduce sub-pressurized gas to the porous medium.

The term 'channel' as used herein is interchangeable with any one or more of the terms port, passage, opening, orifice, pipe and the like.

According to some embodiments, a pressurized gas container is configured to deliver pressurized gas through the gas channel to the porous medium and create an ultra-atmospheric pressure on one side of the porous medium, thereby induce a pressure gradient at the porous medium.

The term 'pressurized gas' as used herein is interchangeable with the term 'compressed gas' and refers to gas under pressure above atmospheric pressure.

According to some embodiments, a vacuum container or sub-atmospheric pressure container is configured to suck gas through the gas channel and create a sub-atmospheric pressure on one side of the porous medium, thereby induce a pressure gradient within the porous medium.

According to some embodiments, the gas channel is connected to a gas source. According to some embodiments, the gas source is a mobile gas source, such as, a gas container. According to some embodiments, the gas source is a gas pump, configured to introduce pressure gradient in the porous medium by pumping gas to or from the gas delivery channel. According to some embodiments, the gas source is a pressurized gas container, configured to contain pressurized gas and to induce a pressure gradient in the porous medium by releasing pressurized gas to the pressurized-gas delivery channel.

According to some embodiments, the nebulizer further comprises an opening configured to deliver the aerosols to a respiratory system of a subject. According to some embodiments, the opening is connected to a nozzle. According to some embodiments, the opening is mechanically connected to a nozzle. According to some embodiments, the nozzle is detachable.

The correlation between droplet size and deposition thereof in the respiratory tract has been established. Droplets around 10 micron in diameter are suitable for deposition in the oropharynx and the nasal area; droplets around 2-4 micron in diameter are suitable for deposition in the central airways (and may be useful for delivering a bronchodilator, such as, salbutamol) and droplets smaller than 1 micron in diameter are suitable for delivery to the alveoli (and may be useful for delivering pharmaceuticals to the systemic circulation, for example, insulin).

According to some embodiments, the at least one pharmaceutical composition comprises one or more pharmaceutically active agents. According to some embodiments, the one or more pharmaceutically active agents are suitable or may be adjusted for inhalation. According to some embodiments, the one or more pharmaceutically active agents are directed for treatment of a medical condition through inhalation.

As used herein, a "pharmaceutical composition" refers to a preparation of a composition comprising one or more pharmaceutically active agents, suitable for administration to a patient via the respiratory system.

According to some embodiments, the pharmaceutical composition further comprises at least one pharmaceutical acceptable carrier. In other embodiments, the pharmaceutical composition may further comprise one or more stabilizers.

According to some embodiments, the nebulizer provides an aerosol containing a therapeutically effective amount of the pharmaceutical composition. As used herein, the term "therapeutically effective amount" refers to a pharmaceutically acceptable amount of a pharmaceutical composition which prevents or ameliorates at least partially, the symptoms signs of a particular disease, for example infectious or malignant disease, in a living organism to whom it is administered over some period of time.

The term "pharmaceutically acceptable" as used herein means approved by a regulatory agency of the Federal or a state government or listed in the U.S. Pharmacopeia or other generally recognized pharmacopeia for use in animals and, more particularly, in humans.

According to some embodiments, the pharmaceutical composition is in a liquid form such as solution, emulsion or suspension. Each possibility represents a separate embodiment of the present invention.

The pharmaceutical compositions of the invention may be prepared in any manner well known in the pharmaceutical art.

Useful pharmaceutically acceptable carriers are well known in the art, and include, for example, lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. Other pharmaceutical carriers can be sterile liquids, such as water, alcohols (e.g., ethanol) and lipid carriers such as oils (including those of petroleum, animal, vegetable or synthetic origin, such as peanut oil, soybean oil, mineral oil, sesame oil and the like), phospholipids (e.g. lecithin), polyethylene glycols, glycerine, propylene glycol or other synthetic solvents. Each possibility represents as separate embodiment of the present invention.

Pharmaceutical acceptable diluents include, but are not limited to, sterile water, phosphate saline, buffered saline, aqueous dextrose and glycerol solutions, and the like. Each possibility is a separate embodiment of the invention.

According to some embodiments, the at least one therapeutic agent is selected from the group consisting of a hormone, a steroid, anti-inflammatory agent, antibacterial agent, anti-neoplastic agent, pain relief agent, narcotics, anti-angiogenic agent, siRNA, immuno-therapy related agent, growth-inhibitory agent, apoptotic agent, cytotoxic agent and chemotherapeutic agent. Each possibility is a separate embodiment of the invention.

According to some embodiments, the at least one pharmaceutical composition comprises albuterol, also known as, salbutamol and Ventolin®.

According to some embodiments, the medical condition is a pulmonary disease. According to some embodiments, the pulmonary disease is bronchospasm, asthma and chronic obstructive pulmonary disease among others. According to some embodiments, the asthma is allergen asthma or exercise-induced asthma.

According to some embodiments, the medical condition is a lung disease affecting the air ways, the alveoli or the interstitium, such as, asthma, chronic obstructive pulmonary disease, chronic bronchitis, emphysema, acute bronchitis, cystic fibrosis, pneumonia, tuberculosis, fragile connections between alveoli, pulmonary edema, lung cancer in its many forms, acute respiratory distress syndrome, pneumoconiosis, interstitial lung disease among others.

According to some embodiments, at least one of the pharmaceutical compositions comprises a therapeutically effective amount of medication for treating one or more of the medical conditions stated hereinbefore.

In some embodiments the medical condition is a metabolic disease, such as, diabetes mellitus (diabetes) Type 1, Type 2 and gestational diabetes, and the at least one pharmaceutical composition comprises a therapeutically effective amount of inhalable insulin.

According to some embodiments, the wetting mechanism is a mechanic mechanism configured to apply pressure onto the liquid absorbing medium. According to some embodiments, the wetting mechanism is a pneumatic mechanism configured to apply pressure onto the liquid absorbing medium. In some embodiment the wetting mechanism is coupled with an actuator. According to some embodiments, the wetting mechanism comprises a metering pump adapted to delivering a pre-determined volume of liquid at desired pressure(s) directly to the surface of the porous medium.

According to some embodiments, the nebulizer is mobile. According to some embodiments, the nebulizer is handheld. According to some embodiments, the nebulizer is powered by a mobile power source.

There is provided, according to some embodiments, a nebulizer housing configured to host at least one cartridge having a liquid absorbing material. The housing may further include any one or more of a porous medium, an opening, a nozzle connected to the opening, one or more container containing liquids, pharmaceutically active agents and composition comprising same, and a combination thereof.

According to some embodiments, the nebulizer housing is mobile. According to some embodiments, the housing is handheld. According to some embodiments, the nebulizer is powered by a mobile power source. According to some embodiments, the cartridge is disposable. According to some embodiments, the cartridge is recyclable. According to some embodiments, the liquid absorbing material is disposable. According to some embodiments, the cartridge is reusable.

According to some embodiments, the nebulizer is configured to communicate wirelessly with servers, databases, personal devices (computers, mobile phones) among others.

According to some embodiments, the nebulizer is assembled by introducing a cartridge into the housing.

There is provided, according to some embodiments, a nebulizer system comprising a housing, an opening in the housing configured to deliver an aerosols to a subject, a receptacle configured to receive a cartridge (the cartridge comprises a liquid absorbing material, and a porous medium, having at least one porous surface, configured to produce aerosols and a wetting mechanism configured to press the liquid absorbing material against the porous medium or against a surface of the porous medium), an actuator configured to control the wetting mechanism and a gas channel, to introduce a pressure gradient to the porous medium.

According to some embodiments, there is provided a nebulizer system comprising a receptacle configured to receive a cartridge. In combination, the nebulizer housing and the cartridge comprise the following elements: a liquid absorbing material, a porous medium having a porous surface, a wetting mechanism and at least one liquid or medication container.

The elements above may be comprised within the housing or the cartridge in various combinations; some examples of these combinations are given below for exemplary purposes, without limiting the disclosure from other possible combinations.

According to some embodiments, the housing comprises a receptacle, a porous medium, a liquid or medication container and a wetting mechanism, while the cartridge comprises a liquid absorbing material.

According to some embodiments, the housing comprises a receptacle, a porous medium and a liquid or medication container, while the cartridge comprises a liquid absorbing material and a wetting mechanism.

According to some embodiments, the housing comprises a receptacle and a liquid or medication container, while the cartridge comprises a porous medium, a liquid absorbing material and a wetting mechanism.

According to some embodiments, the housing comprises a receptacle and a porous medium, while the cartridge comprises a liquid or medication container, a liquid absorbing material and a wetting mechanism.

According to some embodiments, the housing comprises a receptacle while the cartridge comprises a liquid or medication container, a liquid absorbing material a porous medium, and a wetting mechanism.

According to some embodiments, the housing comprises at least two receptacles, a first receptacle configured to receiving a cartridge comprising a liquid absorbing material, and a second receptacle configured to receive a liquid or medication container.

According to some embodiments, the liquid absorbing material is presoaked with medication. According to some embodiments, the presoaked liquid absorbing material is hermetically or semi hermetically sealed. According to some embodiments, the seal is configured to be disrupted or otherwise removed upon usage. According to some embodiments, the seal is configured to be automatically disrupted or otherwise removed, for example, by an actuator in the nebulizer system. According to some embodiments, the seal is configured to be manually removed or disrupted by a user prior to use thereof.

According to some embodiments, the nebulizer system further comprises control mechanism configured to control the release of the liquid from the container containing same, into the liquid absorbing material. According to some embodiments, the control mechanism is configured to control the release of the liquid in a slow and/or gradual release manner According to some embodiments, the nebulizer system further comprises deployment mechanism configured to deploy the medication or liquid from the container containing same and into the liquid absorbing material.

According to some embodiments, the nebulizer system or cartridge comprises a medication preparation mechanism for mixing the medication with a liquid to enable reconstitution of the medication, or dilution thereof, prior to aerosolization of the composition.

According to some embodiments, some mechanisms of the nebulizer system are configured to provide homogeneous or semi homogeneous wetting of the porous medium. According to some embodiments, the mechanisms are other than the liquid absorbing material and the wetting mechanism. Examples for such mechanisms include, but are not limited to, spray mechanism, wiping mechanisms and the like.

Figure 2:
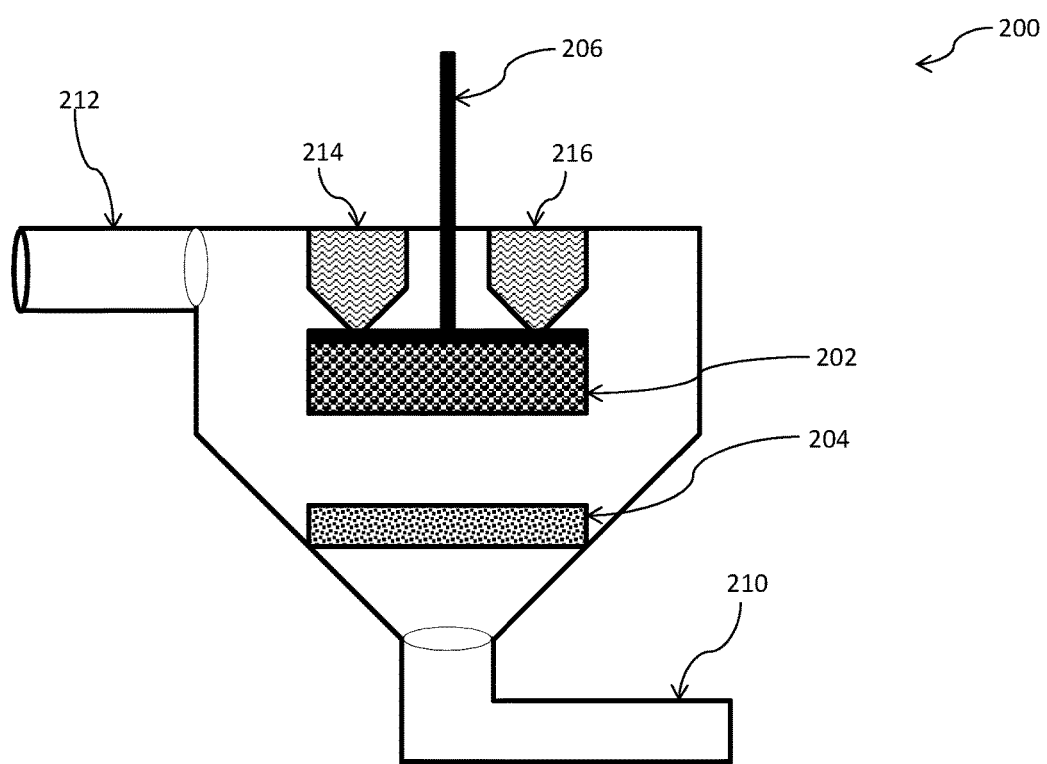
FIG. 2 schematically illustrates a nebulizer with porous medium and medication containers, according to some embodiments.

Reference is now made to FIG. 2, which schematically illustrates a nebulizer 200 comprising a porous medium 204 and a sponge 202, according to some embodiments. Nebulizer 200 further comprises a liquid container 214 and a medication container 216. Liquid container 214 and medication container 216 are configured to enable deployment of their possibly contained contents to sponge 202 to be pressed against porous medium 204.

Figure 3:
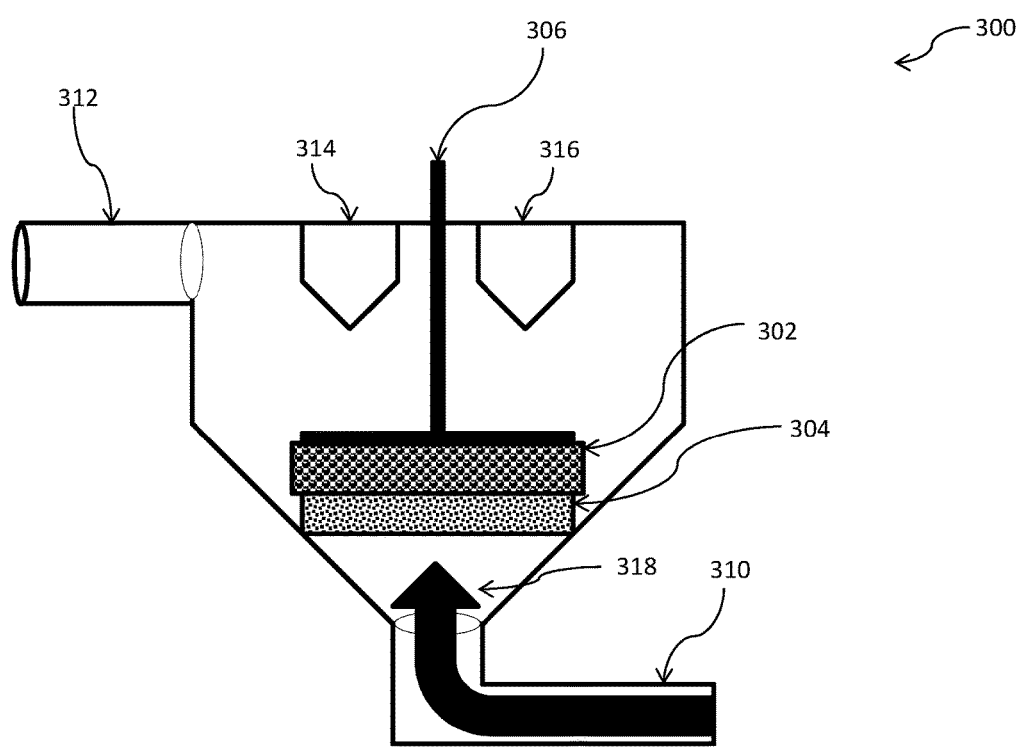
FIG. 3 schematically illustrates a nebulizer with a sponge pressed against a porous medium, according to some embodiments.

Reference is now made to FIG. 3 which schematically illustrates a nebulizer 300 comprising a porous medium 304 and a sponge 302, according to some embodiments. As illustrated, a liquid container 314 and a medication container 316 have had their content deployed to sponge 302, and sponge 302 is pressed against porous medium 304 by a wetting mechanism 306. A pressurized gas 318 is delivered to porous medium 304 via a gas channel 310.

Figure 4:
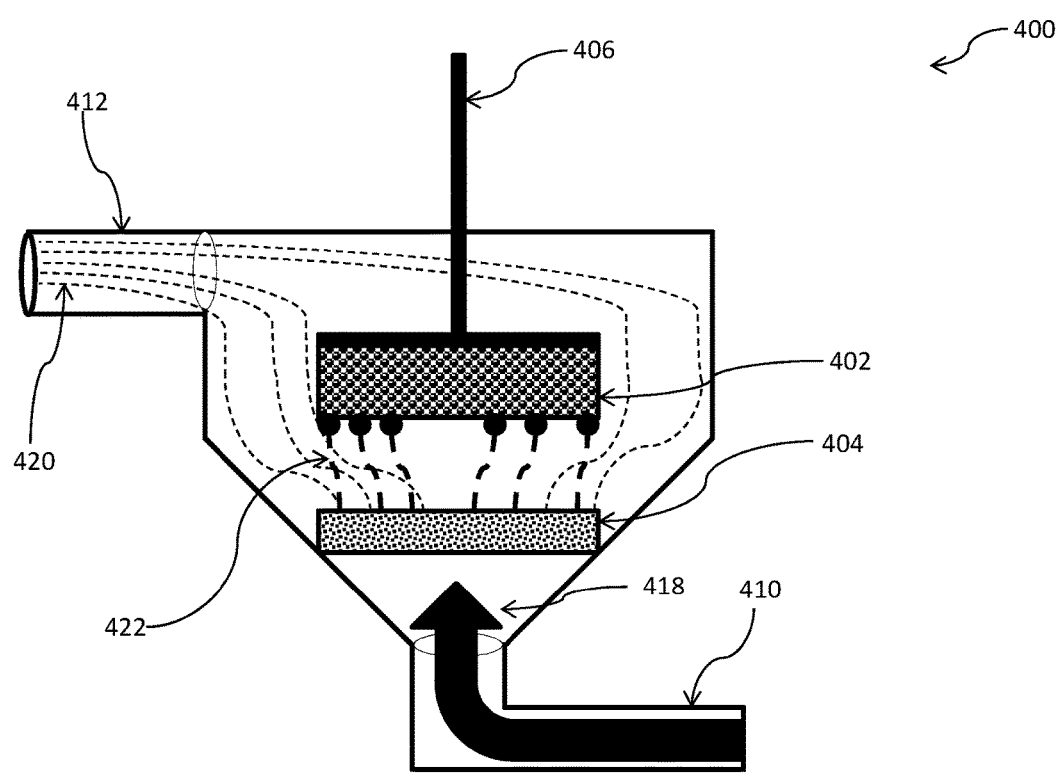
FIG. 4 schematically illustrates generation of aerosol within a nebulizer, according to some embodiments.

Reference is now made to FIG. 4 which schematically illustrates generation of aerosol within a nebulizer, according to some embodiments. A nebulizer 400 is introduced comprising a porous medium 404, a sponge 402 and a nozzle 412, according to some embodiments. Sponge 402 is released from its previous press and wetting position (press and wetting of porous medium 404). A pressurized gas 418 delivered to porous medium 404 via a gas channel 410 introduces a pressure gradient to porous medium 404. The pressure gradient results in the production of an aerosol having large droplets 422 and small droplets 420. Large droplets 422 are impacted by sponge 402 which obstructs their path towards nozzle 412.

Small droplets 420, are lighter than large droplets 422, and are mostly drifted away from impacting sponge 402, thus they are not obstructed and may flow towards nozzle 412. Large droplets 422 are impacted and obstructed by sponge 402, advantageously resulting in a delivery of aerosol characterized with small diameter/size droplets.

The terms 'droplet size' and 'mass median aerodynamic diameter', also known as MMAD, as used herein are interchangeable. MMAD is commonly considered as the median particle diameter by mass.

According to some embodiments, control over droplet size and modality of generated aerosol is achieved by controlling physical properties of the porous medium. According to some embodiments, the physical properties of the porous medium are adjusted based on the desired droplet size. The physical properties of the porous medium, may include, but are not limited to, physical dimensions of the porous medium as a whole, pore count, pore density, pore distribution, pore shape, homogeneity of the aforementioned pore features, hydrophobicity of the porous material, and electromagnetic affinity among other properties. Each possibility is a separate embodiment of the invention.

The term "modality" as used herein refers to the modality of size distributions and includes, but is not limited to, uni-modal, bi-modal and tri-modal size distributions.

According to some embodiments, control over droplet size and modality of generated aerosol is achieved by controlling the physical properties of the liquid absorbing material.

According to some embodiments, control over droplet size and modality of generated aerosol is achieved by controlling the pressure gradient on the porous medium.

According to some embodiments, control over droplet size and modality of generated aerosol is achieved by controlling the properties of the medication and/or liquid and/or composition. The properties of the medication and/or liquid and/or composition which may be adjusted to achieve the desired aerosol, include, but are not limited to, viscosity, surface tension, pH, electrolyte concentration, solid content and polarity According to some embodiments, control over droplet size and modality of generated aerosol is achieved by introducing an impactor. According to some embodiments, the liquid absorbing material is configured to act as an impactor. According to some embodiments, the liquid absorbing material is the impactor. According to some embodiments, control over droplet size of generated aerosol is achieved by introducing a filter. According to some embodiments, the liquid absorbing material is configured to act as a filter. According to some embodiments, the liquid absorbing material is the filter. According to some embodiments, the impactor is an independent structure, different from the liquid absorbing material. According to some embodiments, the filter is an independent structure, different from the liquid absorbing material.

Figure 5:
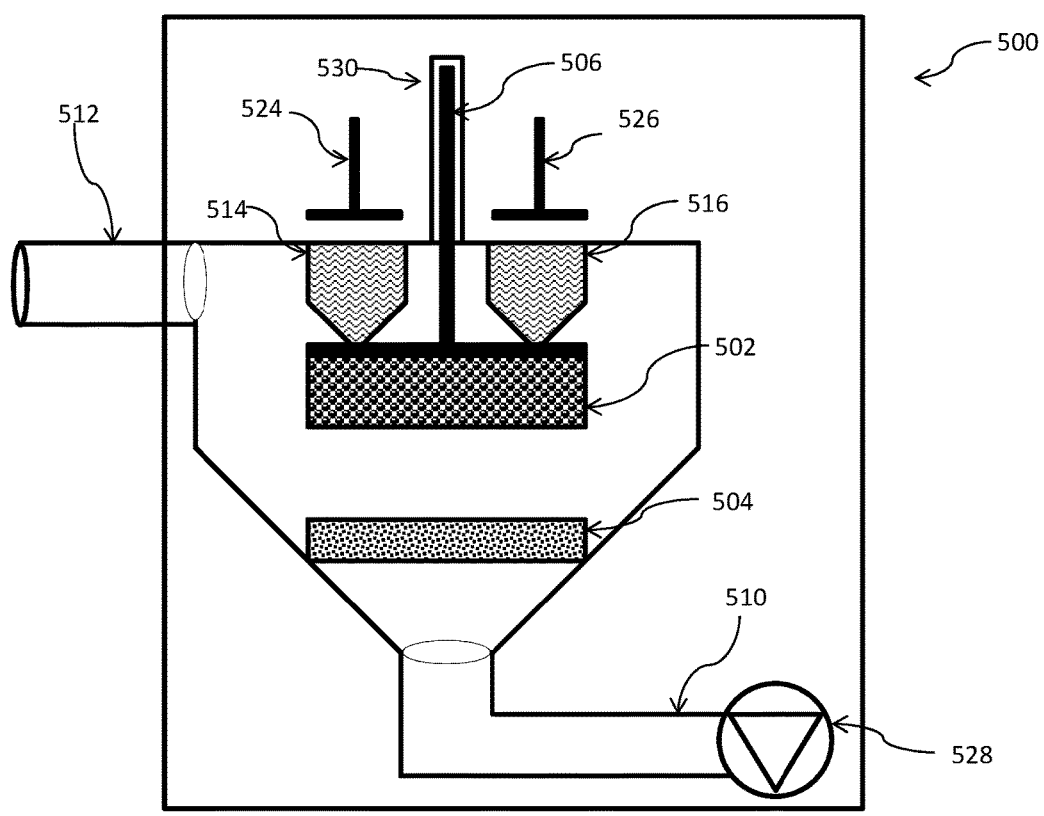
FIG. 5 schematically illustrates a nebulizer system, according to some embodiments.

Reference is now made to FIG. 5 which schematically illustrates a nebulizer system 500, according to some embodiments. Nebulizer system 500 comprises a gas pump 528 an actuator 530 a first deployment controller 524, a second deployment controller 526, a wetting mechanism 506, a sponge 502, a porous medium 504, a gas channel 510, a liquid container 514, a medication container 516 and a nozzle 512.

According to some embodiments, pump 528 is configured to deliver compressed gas to porous medium 504 via gas channel 510. Actuator 530 is configured to control the movement and function of wetting mechanism 506 for pressing sponge 502 against porous medium 504. First deployment controller 524 is configured to control the deployment of contained liquid in liquid container 514 to sponge 502, and second deployment controller 526 is configured to control the deployment of medication in medication container 516 to sponge 502.

According to some embodiments, the actuator is configured to control the pressure applied onto the liquid absorbing material. According to some embodiments, the actuator is configured to control the movement of the wetting mechanism. According to some embodiments, the actuator operates through mechanic, electro mechanic, electromagnetic, electro thermal, hydraulic, pneumatic or electronic mechanism. Each possibility is a separate embodiment of the invention.

There is provided, according to some embodiments, a method for producing aerosol comprising the steps of providing a liquid absorbing material, a porous medium having two sides in which the first side is facing the liquid absorbing material and further providing liquid, wetting the liquid absorbing material with the liquid, pressing liquid absorbing material against the porous medium, introducing pressure gradient to the porous medium and producing aerosol at the first side of the porous medium, the produced aerosol comprises droplets of the liquid.

According to some embodiments, the liquid is provided in a container. According to some embodiments, the method further comprises controlling the release of the liquid from the container into the liquid absorbing material. According to some embodiments, the method further comprises releasing the liquid in a slow and/or gradual release manner. According to some embodiments, the method further comprises deploying the medication or liquid from the container and into the liquid absorbing material.

According to some embodiments, the method further comprises providing a first container with a liquid and a second container with medication, and mixing the medication with the liquid to enable reconstitution of the medication, or dilution thereof, prior to aerosolization.

The term 'wetting' as used herein refers to homogenous or pseudo homogenous wetting of one side of the porous medium.

According to some embodiments, the method further comprises wetting the porous medium homogenously.

According to some embodiments, the method further comprises providing a pharmaceutical composition and mixing the pharmaceutical composition with the liquid, prior to wetting the liquid absorbing agent.

According to some embodiments, the liquid absorbing material already includes a pharmaceutical composition. The pharmaceutical composition within the liquid absorbing material may be in a solid form, e.g. a powder, or otherwise concentrated, such that upon wetting the liquid absorbing material, the pharmaceutical composition is reconstituted, or otherwise diluted, thereby resulting with the required pharmaceutically acceptable form suitable for inhalation following the conversion thereof into aerosols.

According to some embodiments, the liquid mixed with the pharmaceutical composition is a pharmaceutically acceptable carrier.

According to some embodiments, the pressing of the liquid absorbing material upon the porous medium is iterated a plurality of times. According to some embodiments, the pressing is executed while applying a non-constant pressing force/pressure across iterations. According to some embodiments, after deploying a content of liquid or medication container into the liquid absorbing material, a first pressing of the liquid absorbing material against the porous medium is carried out utilizing a first pressing force (pressure), a second pressing of the liquid absorbing material against the porous medium is executed utilizing a second pressing force, and so on. According to some embodiments, the first pressing force is lower than the second pressing force, advantageously resulting in a more unified wetting of the porous surface of the porous medium.

In some embodiments, a deployment of medication into the liquid absorbing material is performed, then the liquid absorbing material is pressed against the porous medium, wetting the porous surface of the porous medium for generating aerosol, and then a deployment of a liquid into the liquid absorbing material is performed. According to some embodiments, the liquid is sterile. According to some embodiments, the liquid is saline, water, carrier, cleansing liquid and the like, the deployment of which is performed for diluting the medication content in the liquid absorbing material. In some embodiment, the deployment of the liquid is performed for cleansing the liquid absorbing material and releasing the medication residues that may accumulate in the liquid absorbing material to achieve better delivery of medication to the subject, or for cleansing the liquid absorbing material, the porous medium or both.

According to some embodiments, by cleansing the liquid absorbing material, the porous medium or both, the components may be reused. Advantageously, the cleansing may prevent accumulation of medication residue in the nebulizer or some components thereof.

According to some embodiments, the droplets of the aerosol produced by the method and nebulizers disclosed herein are having an MMAD within the range of 0.3 to 7 microns. According to some embodiments, the MMAD is within the range of 2 to 10 microns. According to some embodiments, the MMAD is less than 5 microns.

According to some embodiments, the wetting mechanism includes a rotatable/displaceable elongated member, configured to be movably placed on the surface of the porous medium, or in close proximity thereto, or placed on the liquid absorbing material. According to some embodiments, the wetting mechanism includes a rotatable/displaceable elongated member (e.g. a spinning magnet) configured to be placed on the liquid absorbing material, such that liquid is extracted from the liquid absorbing material by the wetting mechanism. According to some embodiments, the rotatable elongated member is configured to move across the surface of the porous medium, thereby to homogeneously or semi-homogeneously spread the liquid on the surface of the porous medium.

According to some embodiments, the elongated member is axially movable. According to some embodiments, the elongated member is movable to cover the entire surface of the porous medium or substantial portions thereof. According to some embodiments, the wetting mechanism further includes an actuator, configured to displace/move or induce the displacement/movement of the elongated member.

The term "substantial portions" as used herein commonly refers to at least 30% coverage of the surface of the porous medium. According to some embodiments, the substantial portions include at least 50% coverage of the surface of the porous medium, at least 60% coverage of the surface of the porous medium, at least 70% coverage of the surface of the porous medium, at least 80% coverage of the surface of the porous medium or at least 90% coverage of the surface of the porous medium.

According to some embodiments, the elongated member may include a magnet, and the actuator may also include a magnet, magnetically associated with the magnet of the elongated member, such that by moving/displacing the magnet/electromagnet of the actuator, a moving/displacing of the elongated member may be induced.

According to some embodiments, one or more of the magnets includes an electromagnet. According to some embodiments, the actuator may include a motor configured to move/displace the actuating magnet.

According to some embodiments, the elongated member may be coated by a hydrophobic coating. According to some embodiments, the elongated member may be at least partially coated by a hydrophobic coating. According to some embodiments, the coating may be smooth, non-corrosive, non-toxic, non-evaporative or a combination thereof. According to some embodiments, the coating may include polytetrafluoroethylene (e.g. Teflon®).

The term "at least partially" as used herein may include at least 50% coating of the elongated member, at least 60% coating of the elongated member, at least 70% coating of the elongated member, at least 80% coating of the elongated member or at least 90% coating of the elongated member.

According to some embodiments, the elongated member is an elongated tubular member. According to some embodiments, the elongated member may be movable by an actuator, mechanically connected thereto. According to some embodiments, the elongated member may be movable by an air-flow within the nebulizer and/or through the porous material.

According to some embodiments, the elongated member may be a roller. According to some embodiments, the elongated member may be a smearing device. According to some embodiments, the elongated member may be a spreading device. According to some embodiments, the elongated member may be configured to force at least portions of the liquid to at least some of the pores of the porous medium.

Figure 9A:
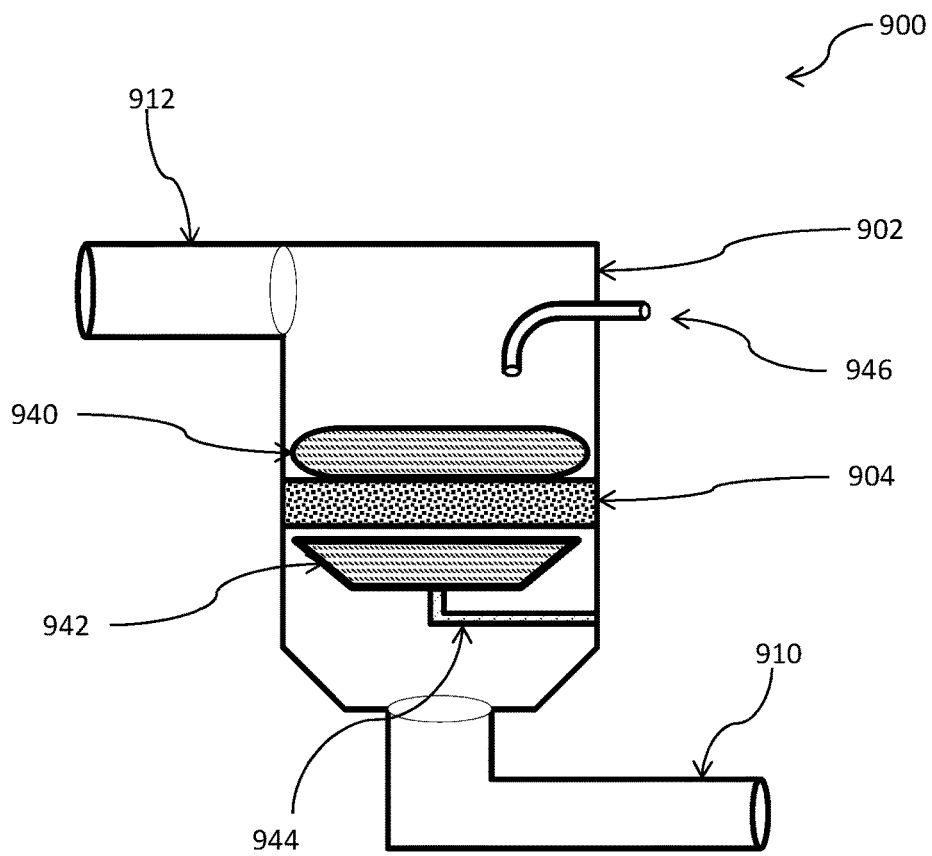
FIG. 9a schematically illustrates a nebulizer with a rotatable wetting mechanism and a bottom actuator at side cross section, according to some embodiments.

Reference is now made to FIG. 9a, which schematically illustrates a side cross section of a nebulizer 900 with a rotatable wetting mechanism, according to some embodiments. According to some embodiments, the wetting mechanism of nebulizer 900 includes a rotatable elongated member, such as movable magnet 940, which is placed on, or in close proximity to a surface of a porous medium, such as porous disc 904, within a nebulizer housing, such as housing 902. Movable magnet 940 is configured to rotate on porous disc 904, thereby homogeneously or semi-homogeneously spread a liquid on porous disc 904 and/or at least partially force a liquid within the pores of porous disc 904. According to some embodiments, nebulizer 900 further includes a liquid deploying mechanism, such as medication conduit 946, configured to provide liquids and/or medication(s) to movable magnet 940 and/or porous disc 904. According to some embodiments, nebulizer 900 further includes an actuator configured to directly or indirectly move or induce the displacement of movable magnet 940. According to some embodiments, the actuator includes a motor 944, mechanically or electromechanically connected to an actuator-magnet, such as motor-magnet 942 being associated with movable magnet 940, such that a displacement of motor-magnet 942 induces a displacement of movable magnet 940. Motor 944 is configured to axially rotate motor-magnet 942, thereby induce an axial rotation of movable magnet 940 over/on the surface of porous medium 904.

In operation, according to some embodiments, pressurized gas/air is provided to housing 902, for example through pressurized-gas conduit 910, and introduced to one side of porous disc 904 which interrupts the flow of gasses therethrough, thereby a pressure gradient occurs across porous disc 904. Liquids may be provided through medication conduit 946 and introduced to the surface of porous disc 904, and then movable magnet 940 spreads the liquid homogeneously or semi-homogeneously on the surface and at least partially forced through the pores of porous disc 904 by the axial rotation thereof, induced by the rotation of motor magnet 942 and motor 944. According to some embodiments, the pressure gradient on porous disc 904 generates a mist of multiple droplets as the gas passes through the pores, the mist is then delivered through an outlet, such as mouthpiece 912.

Reference is now made to FIG. 9*b*, which schematically illustrates a top cross section view of a nebulizer 901 with a rotatable wetting mechanism, according to some embodiments. The rotatable wetting mechanism includes a displaceable/movable elongated member, such as a movable magnet 940, which is placed on, or in close proximity to a surface of a porous medium, such as a porous disc 904 held within a nebulizer housing 902. Movable magnet 940 is configured to be rotatable (arrows 950) and to spread/smear/distribute liquids on the surface of porous disc 904, the liquids may be provided onto the surface of porous disc 904, and According to some embodiments, the liquids may be provided to rotatable magnet 940.

Reference is now made to FIG. 9*c*, which schematically illustrates a side cross section of a nebulizer 900 with a rotatable wetting mechanism and a peripheral actuator, according to some embodiments. According to some embodiments, the wetting mechanism of nebulizer 900 includes a rotatable elongated member, such as movable magnet 940, which is placed on, or in close proximity to a surface of a porous medium, such as porous disc 904, within a nebulizer housing, such as housing 902. Movable magnet 940 is configured to rotate on porous disc 904, thereby homogeneously or semi-homogeneously spread a liquid on porous disc 904 and/or at least partially force a liquid into the pores of porous disc 904. According to some embodiments, nebulizer 900 further includes a liquid deploying mechanism, such as medication conduit 946, configured to provide liquids and/or medication(s) to movable magnet 940 and/or porous disc 904. According to some embodiments, nebulizer 900 further includes a peripheral actuator configured to directly or indirectly move or induce the displacement of movable magnet 940. According to some embodiments, the peripheral actuator included is configured to be placed over, or to surround, movable magnet 940 and to fluctuate the magnetic field flux near movable magnet 940, thereby induce a mechanical movement thereof (rotation). According to some embodiments, the peripheral actuator may be a ring actuator such as controllable electromagnet-ring 960 which may include a plurality of controllable electro-magnets (not shown) which are electrically controlled for inducing a gradient in the electromagnetic field flux in the environment of movable magnet 940, thereby induce an axial rotation of movable magnet 940 over/on the surface of porous medium 904.

Figure 9B:
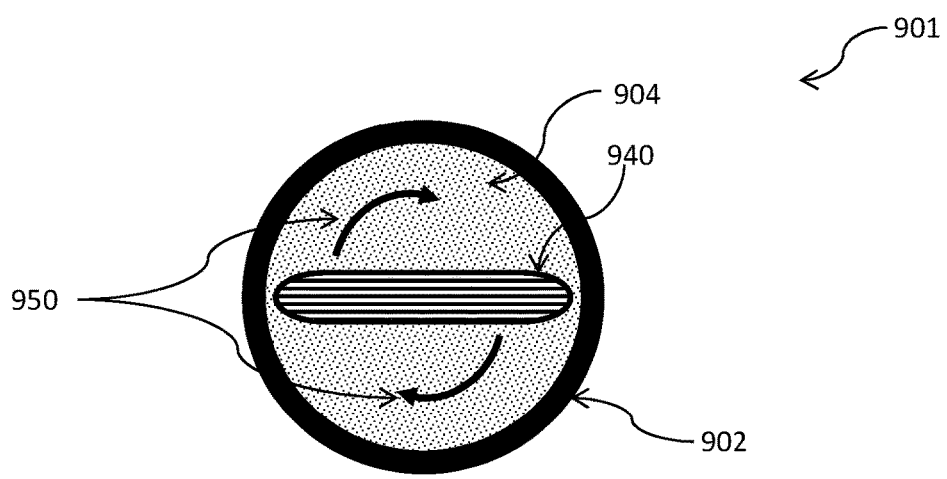
FIG. 9b schematically illustrates a nebulizer with a rotatable wetting mechanism and a bottom actuator at top cross section, according to some embodiments.
Figure 9C:
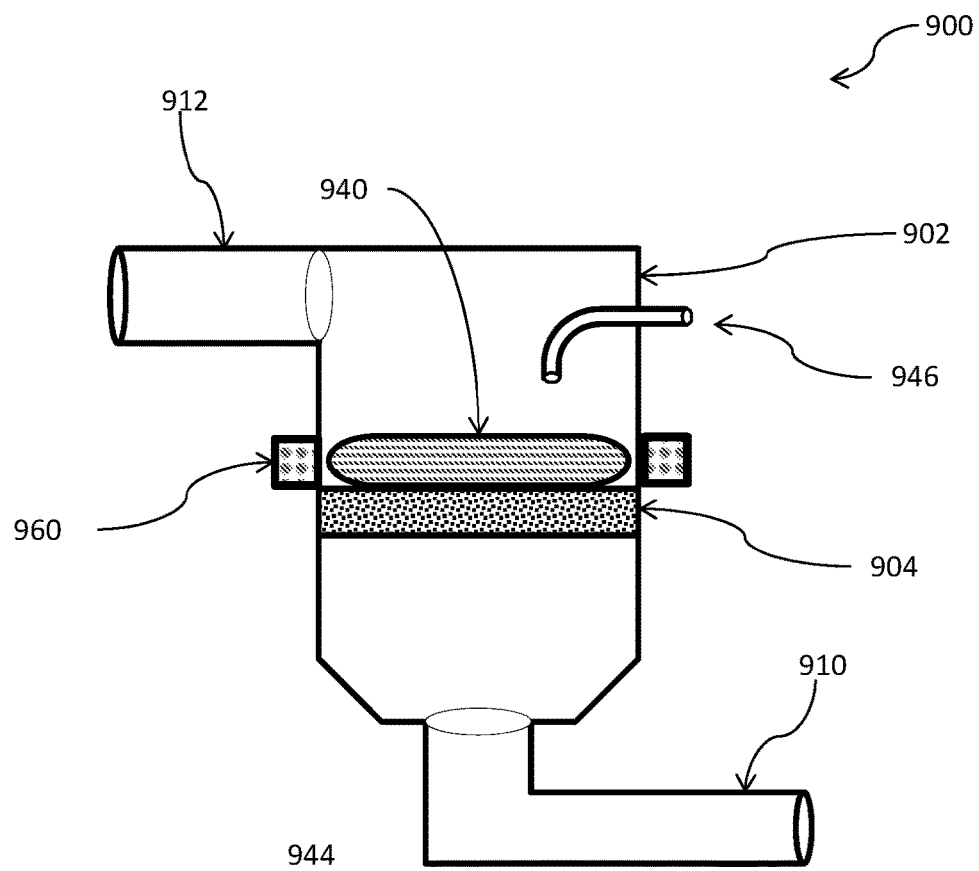
FIG. 9c schematically illustrates a nebulizer with a rotatable wetting mechanism and a peripheral actuator at side cross section, according to some embodiments.
Figure 9D:
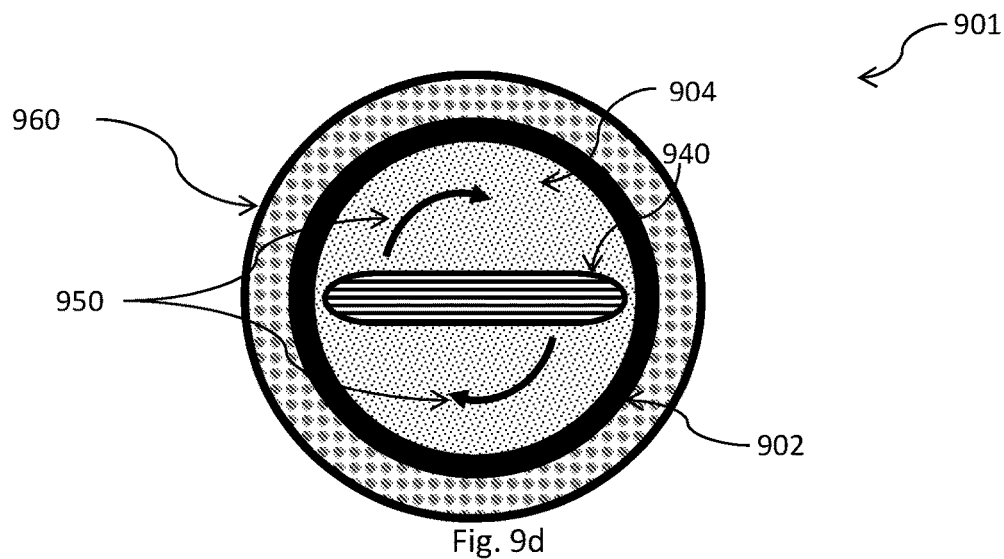
FIG. 9d schematically illustrates a nebulizer with a rotatable wetting mechanism and a peripheral actuator at top cross section, according to some embodiments.

Reference is now made to FIG. 9d, which schematically illustrates a top cross section view of a nebulizer 901 with a rotatable wetting mechanism, according to some embodiments. The rotatable wetting mechanism includes a displaceable/movable elongated member, such as a movable magnet 940, which is placed on, or in close proximity to a surface of a porous medium, such as a porous disc 904 held within a nebulizer housing 902. According to some embodiments, nebulizer 901 may also include a peripheral actuator configured to induce a change in the magnetic field flux in the environment of movable magnet 940 thereby induce a rotatable movement thereof 950. According to some embodiments, peripheral actuator may be a ring actuator such as controllable electromagnet-ring 960. According to some embodiments, movable magnet 940 is configured to be rotatable (arrows 950) and to spread/smear/distribute liquids on the surface of porous disc 904, the liquids may be provided onto the surface of porous disc 904, and According to some embodiments, the liquids may be provided to rotatable magnet 940.

Figure 9E:
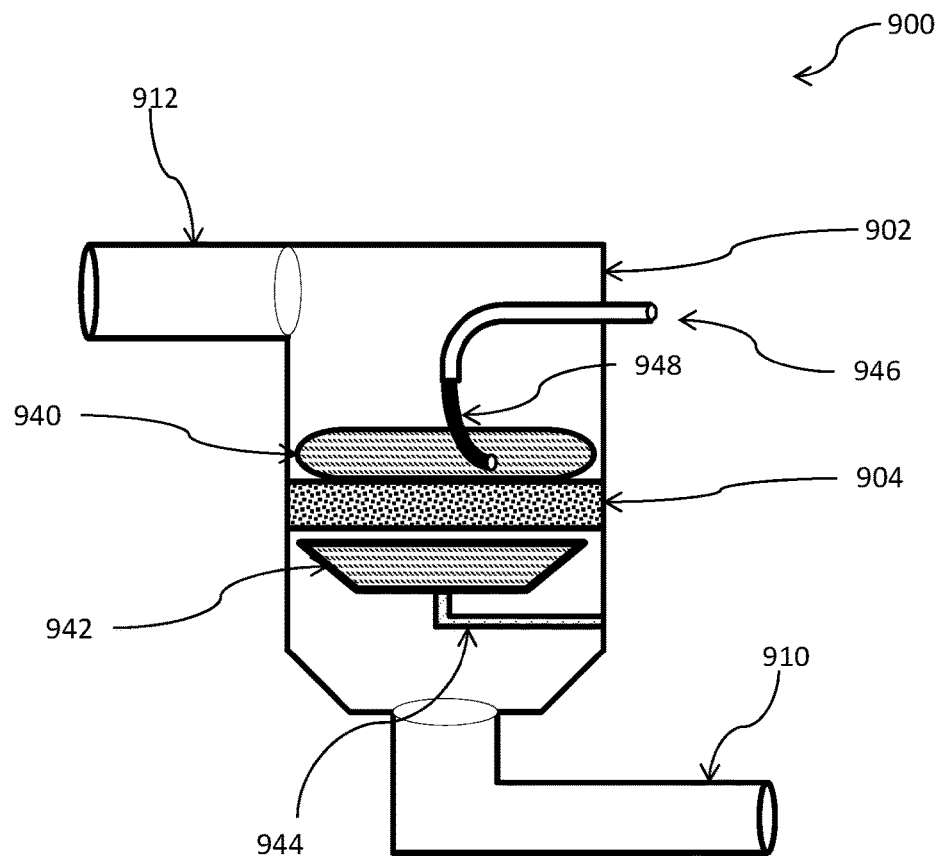
FIG. 9e schematically illustrates a nebulizer with a rotatable wetting mechanism and a flexible medication deploying end at side cross section, according to some embodiments.

Reference is now made to FIG. 9e, which schematically illustrates a side cross section of a nebulizer 900 with a rotatable wetting mechanism, according to some embodiments. According to some embodiments, nebulizer 900 is essentially similar to the nebulizer of FIG. 9a, and further includes a flexible medication deploying end, such as flexible-conduit 948 which is connected to medication conduit 946 and is configured to provide/deploy medication on porous disc 904 According to some embodiments, flexible-conduit 948 is configured to reach near the surface of porous disc 904, and to be flexibly movable by the rotation of movable magnet 940 for deploying medication at close proximity to the surface of porous disc 904 without obstructing the rotation/axial-movement thereof.

According to some embodiments, deploying medication near the surface of porous disc 904 via a flexible member, such as flexible-conduit 948, may provide a homogeneous spreading of medication on the surface of porous disc 904.

Figure 9F:
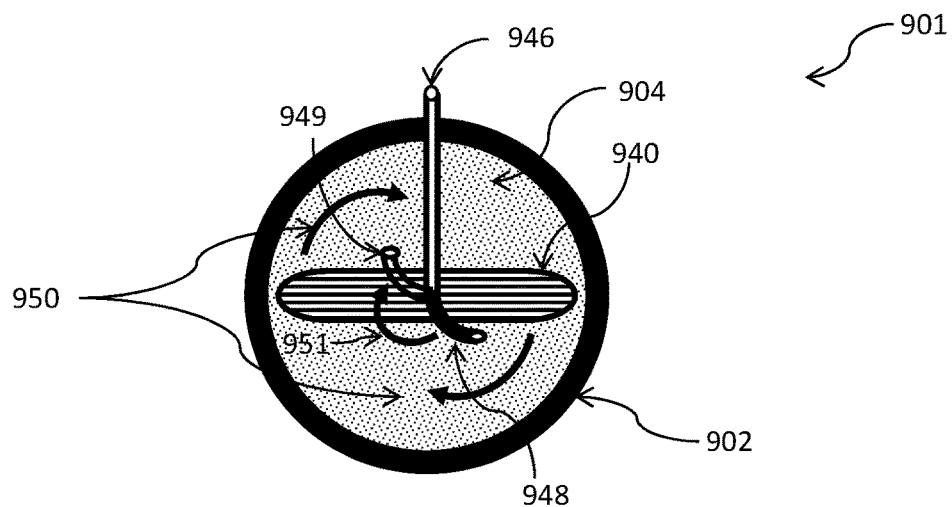
FIG. 9f schematically illustrates a nebulizer with a rotatable wetting mechanism and a flexible medication deploying end at top cross section, according to some embodiments.

Reference is now made to FIG. 9f, which schematically illustrates a top cross section view of a nebulizer 901 with a rotatable wetting mechanism, according to some embodiments. The rotatable wetting mechanism includes a displaceable/movable elongated member, such as a movable magnet 940, which is placed on, or in close proximity to a surface of a porous medium, such as a porous disc 904 held within a nebulizer housing 902. Movable magnet 940 is configured to be rotatable (arrows 950) and to spread/smear/distribute liquids on the surface of porous disc 904, the liquids may be provided onto the surface of porous disc 904, and According to some embodiments, the liquids may be provided to rotatable by a flexible medication deploying member, such as flexible-conduit 948 shown at a first location, and is flexibly movable (arrow 951) to a second location 949 by the rotation of movable magnet 940.

Figure 9G:
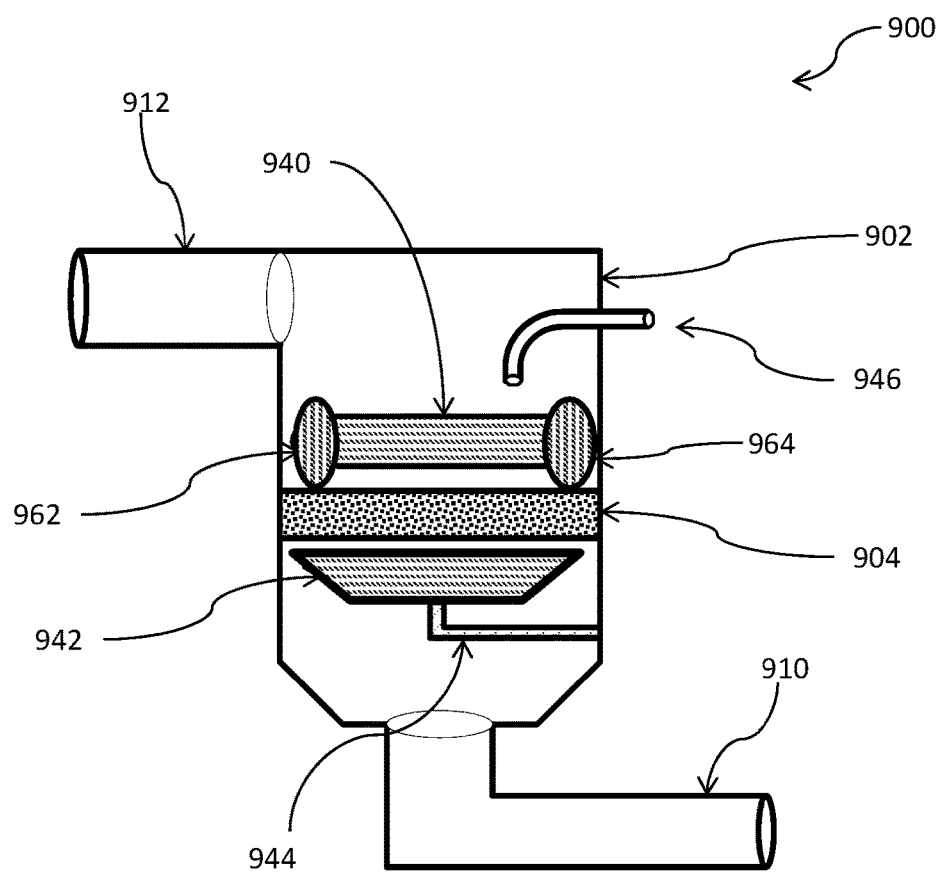
FIG. 9g schematically illustrates a nebulizer with a rotatable wetting mechanism having protruding ends at side cross sections, according to some embodiments.

Reference is now made to FIG. 9g, which schematically illustrates a side cross section of a nebulizer 900 with a rotatable wetting mechanism, essentially as described in FIG. 9a, according to some embodiments. According to some embodiments, nebulizer 900 further includes two spacers mounter/fastened on movable magnet 940, such as a first Teflon™ ball 962 and second Teflon™ ball 964, each being mechanically connected to one end of movable magnet 940 for elevating it from the surface of porous disc 904 and thereby improve the homogeneous spreading of the liquid and lead to production of controllable aerosol droplet size.

According to some embodiments, the two spacers may be integrally formed with the movable magnet. According to some embodiments, the two spacers are protrusions at the two ends of the movable magnet.

Figure 9H:
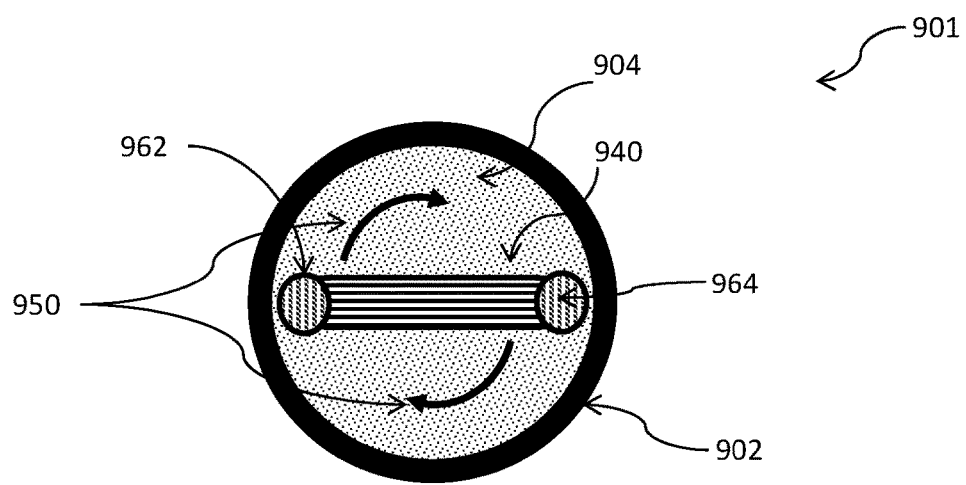
FIG. 9h schematically illustrates a nebulizer with a rotatable wetting mechanism having protruding ends at top cross section, according to some embodiments.

Reference is now made to FIG. 9h, which schematically illustrates a top cross section of a nebulizer 900 with a rotatable wetting mechanism, essentially as described in FIG. 9b, according to some embodiments. Depicted in FIG. 9h are first Teflon™ ball 962 and second Teflon™ ball 964, each being mechanically connected to one end of movable magnet 940 to prevent direct contact thereof with the surface of porous disc 904.

Figure 9I:
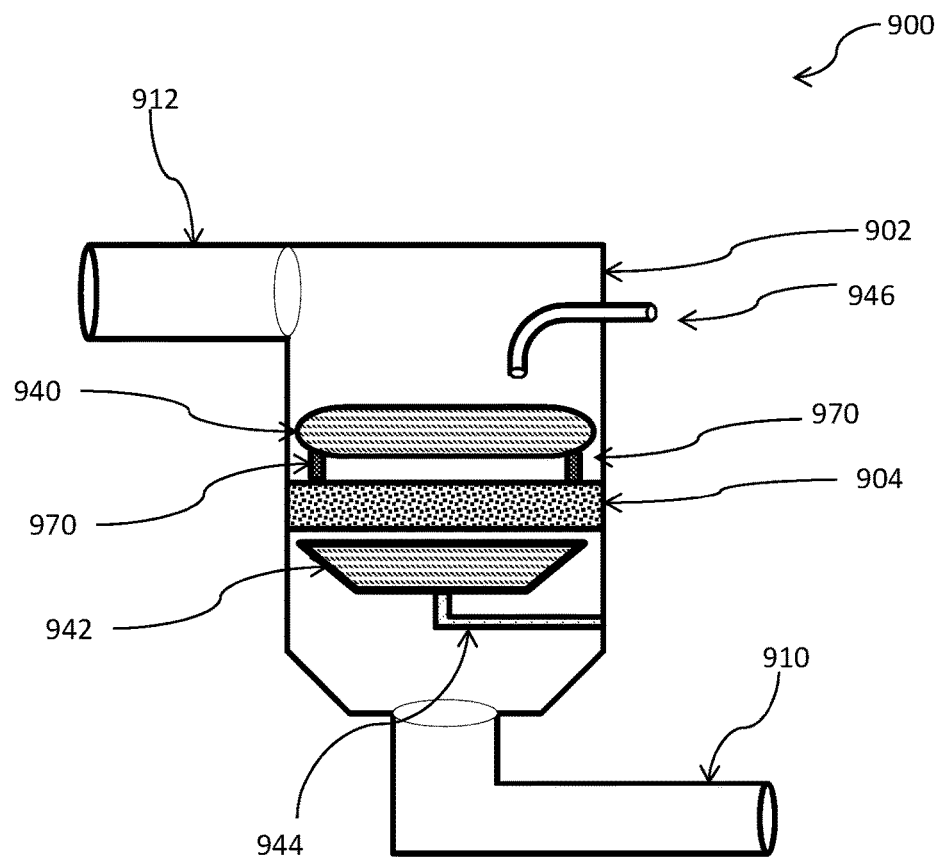
FIG. 9i schematically illustrates a nebulizer with a rotatable wetting mechanism and a spacer at side cross sections, according to some embodiments.

Reference is now made to FIG. 9i, which schematically illustrates a side cross section of a nebulizer 900 with a rotatable wetting mechanism, essentially as described in FIG. 9a, according to some embodiments. According to some embodiments, nebulizer 900 further includes a spacer placed/mounted/integrated on the surface of porous disc 904, such as a Teflon-ring 970 which is configured to elevate movable magnet 940 above the surface of porous medium 904 for providing spacing and preventing a direct contact therebetween. According to some embodiments, movable magnet 940 is tightened to Teflon-ring 970, and is pulled towards porous disc by the magnetic field applied by motor magnet 942. According to some embodiments, Teflon-ring 970 is configured to facilitate low-friction movement of movable magnet 940 thereon.

Figure 9J:
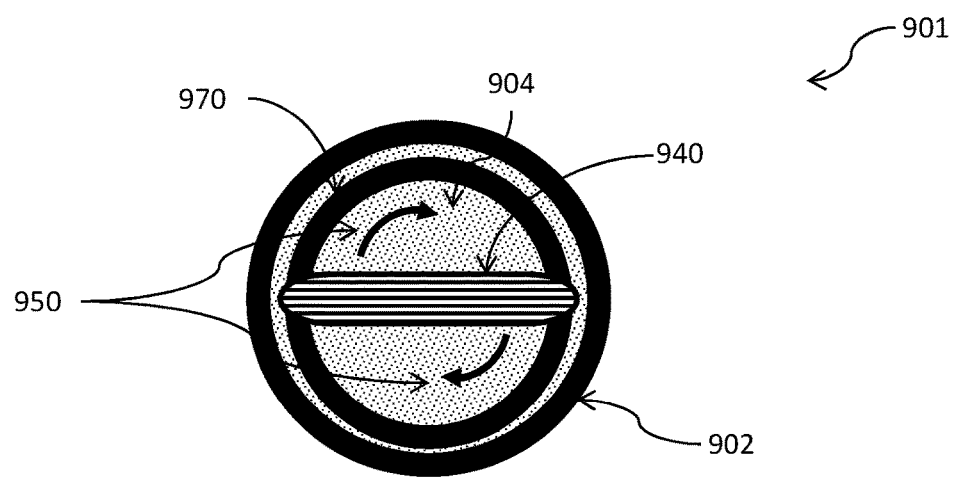
FIG. 9j schematically illustrates a nebulizer with a rotatable wetting mechanism and a spacer at top cross sections, according to some embodiments.

Reference is now made to FIG. 9j, which schematically illustrates a top cross section of a nebulizer 900 with a rotatable wetting mechanism, essentially as described in FIG. 9b, according to some embodiments. Depicted in FIG. 9j is Teflon-ring 970 placed on the surface of porous disc 904, to prevent direct contact thereof with the movable magnet 940.

According to some embodiments, the spacing/distance/elevation between the surface of the porous medium and the movable magnet is approximately 100 micron (0.1 μm). According to some embodiments, the spacing/distance/elevation between the surface of the porous medium and the movable magnet is in the range of 50 micron (0.05 μm) to 150 micron (0.15 μm). According to some embodiments, the spacing/distance/elevation between the surface of the porous medium and the movable magnet is in the range of 20 micron (0.02 μm) to 200 micron (0.2 μm).

According to some embodiments, the term "approximately" may refer to the distance between the surface of the porous medium and the movable magnet, an thus may refer to values within the range of 20% or less from the value indicated. For example, a spacing/distance/elevation of approximately 100 micron (0.1 μm) includes values within the range of 80-100 micron.

Without being bound by any theory or mechanism of action, the distance between the surface of the porous medium and the movable magnet seems to result with advantageous droplet size distribution, possible due to an improved wetting mechanism.

Figure 10:
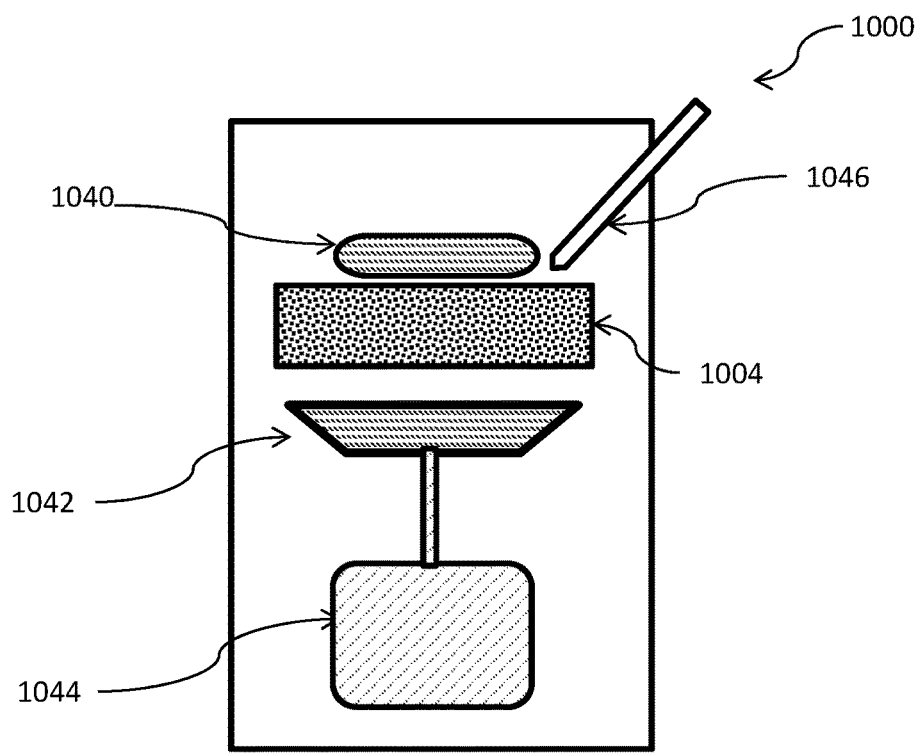
FIG. 10 schematically illustrates nebulizer with a rotatable wetting mechanism and a liquid deploying structure, according to some embodiments.

Reference is now made to FIG. 10, which schematically illustrates nebulizer 1000 with a rotatable wetting mechanism and a liquid deploying structure 1046, according to some embodiments. Liquid deploying mechanism, such as liquid conduit 1046 is configured to deploy/provide liquids to the surface of a porous medium 1004 and a rotatable magnet 1040 is placed on the surface of porous medium 1004 and is configured to be movable thereon and to homogeneously or semi-homogeneously spread the liquids provided by liquid conduit 1046 on the surface of porous medium 1004. The wetting mechanism further comprises an actuator having, according to some embodiments, a control-magnet 1042 magnetically/mechanically associated with rotatable magnet 1040 and rotated by a motor 1044.

When a pressure gradient is applied on porous medium 1004, a mist/aerosol of multiple droplets is released from the wetted/damped/moistened surface of porous medium 1004.

According to some embodiments, motor 1044 may comprise a brushed or brushless DC motor, for example a steppe moto or the like. According to some embodiments, motor 1044 may comprise an AC motor, such as an induction motor or the like.

Figure 11:
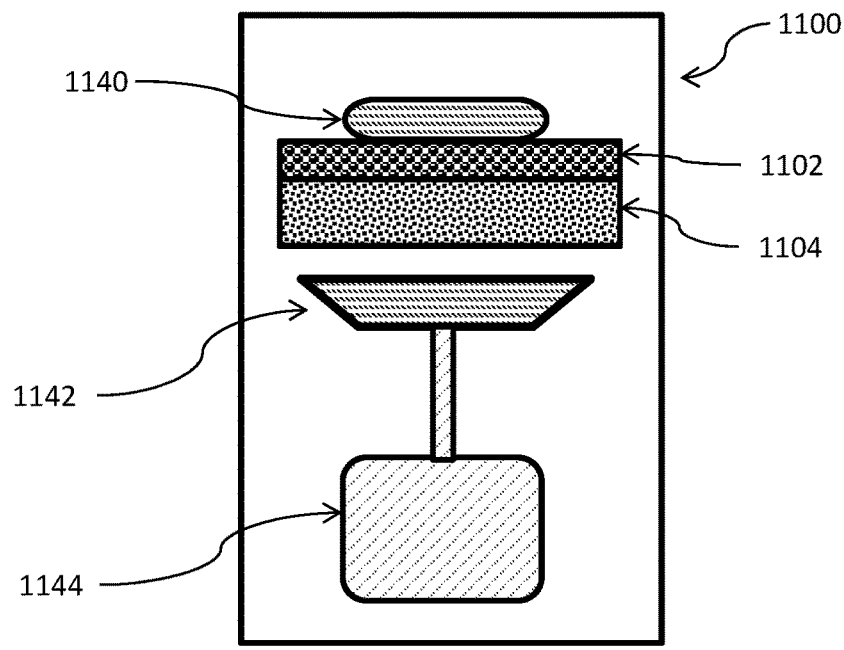
FIG. 11 schematically illustrates nebulizer with a rotatable wetting mechanism and a liquid absorbing material, according to some embodiments.

Reference is now made to FIG. 11, which schematically illustrates a nebulizer 1100 with a rotatable wetting mechanism and a liquid absorbing material, such as sponge 1102, according to some embodiments. Liquid absorbing material is placed on a surface of a porous medium 1104 and configured to reversibly contain/absorb liquids, and release the liquids with changed physical conditions such as pressing. A movable elongated spreader/presser, such as rotating rod 1140, is placed on sponge 1102 and is configured to press at least some portions thereof against the surface of porous medium 1104, thereby force the release of absorbed liquids from sponge 1102. The moving of rotating rod 1140 is induced/caused by the rotating displacement of an actuator that is mechanically and/or magnetically associated with rotating rod 1140. According to some embodiments, rotating rod 1140 may be movable/rotatable by inducing magnetic field changes in the environment thereof, and the actuator includes a magnetic-field inducer 1142 rotatable by a motor 1144 and configured to induce the rotation/displacement of rotating rod 1140 on sponge 1102 thereby pressing against various areas thereon and controllably releasing liquid to the surface of porous medium 1104.

When a pressure gradient is applied on porous medium 1104, a mist/aerosol of multiple droplets is released from the wetted/damped/moistened surface of porous medium 1104.

Figure 12:
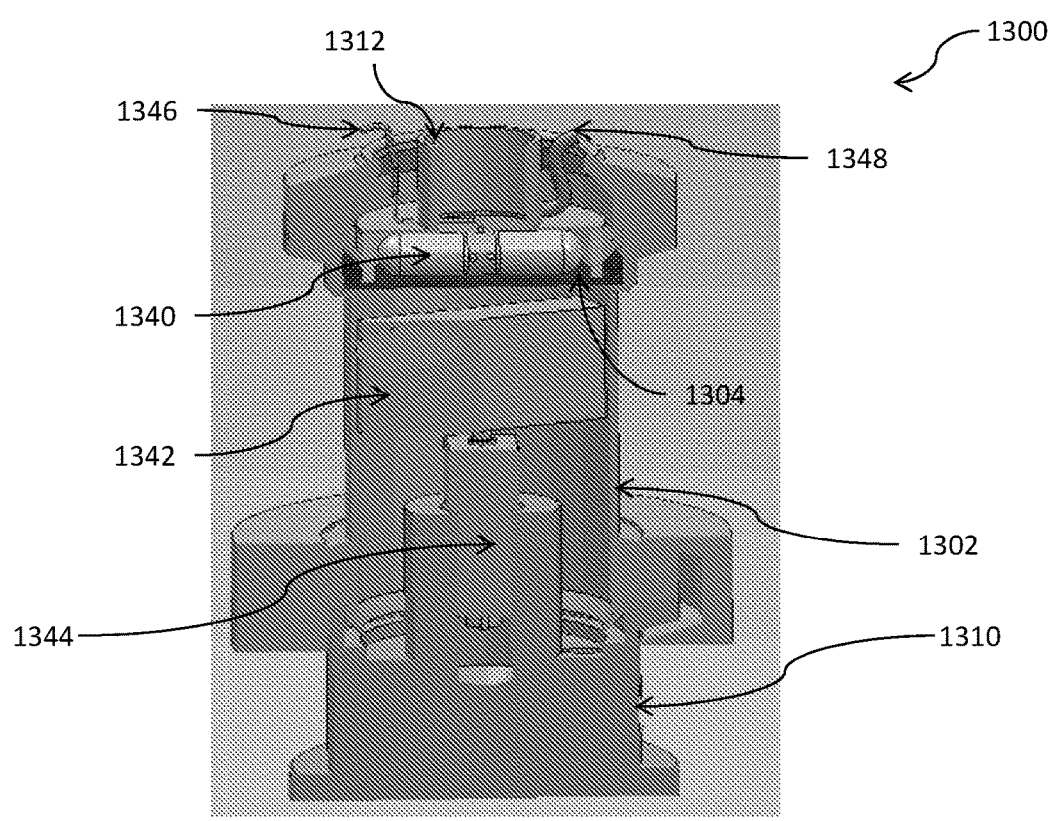
FIG. 12 schematically illustrates a side cross section of a nebulizer assembly including an aerosolizing cartridge comprising a rotatable wetting mechanism, according to some embodiments.

Reference is now made to FIG. 12, which schematically illustrates a side cross section of a nebulizer assembly 1300 with a rotatable wetting mechanism, according to some embodiments. Nebulizer 1300 includes a housing 1302 with an inlet orifice 1310, an outlet orifice 1312, a liquid conduit 1346 and a pressure-sensor conduit 1348. Nebulizer 1300 further includes a rotatable spreading mechanism, such as spreading elongated magnet 1340 placed on a surface of a porous disc 1304 for spreading liquids thereon, an actuator within housing 1302 is associated with spreading elongated magnet 1340, the actuator includes a motor 1344 mechanically connected to a motor-magnet 1342 and is configured to rotate spreading elongated magnet 1340 for spreading liquids on the surface and/or through the pores of porous disc 1304. According to some embodiments, liquid conduit 1346 is configured to provide liquids to a central section of spreading elongated magnet 1340.

Figure 13:
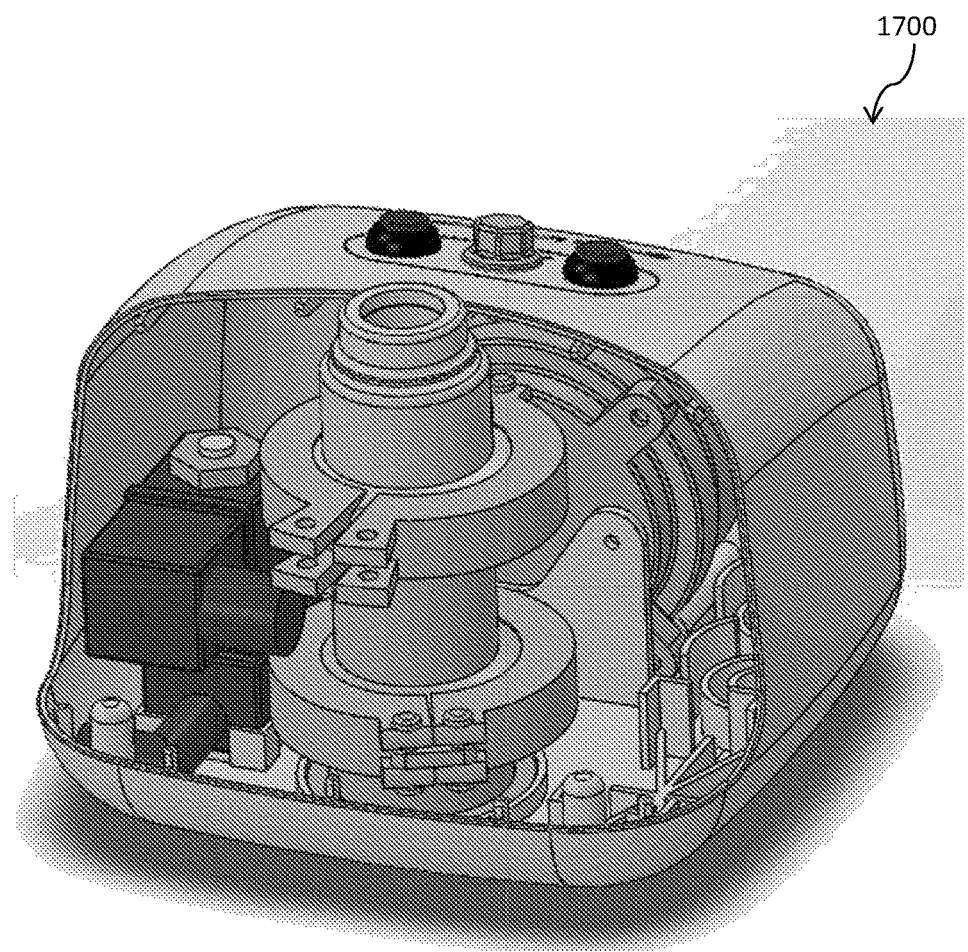
FIG. 13 schematically illustrates a nebulizer system assembly with a rotatable wetting mechanism, according to some embodiments.

Reference is now made to FIG. 13, which schematically illustrates a nebulizer system assembly 1700 with a rotatable wetting mechanism, according to some embodiments. Nebulizer system assembly 1700 includes various functional, control and/or indicatory components. For exemplary purposes, system assembly 1700 includes a nebulizer, a gas pump for providing pressurized gas to the nebulizer, a pressure sensor, control gauges and buttons and others.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

EXAMPLES

Example 1—Measurements of Water Aerosol Droplet Diameter

Figure 6:
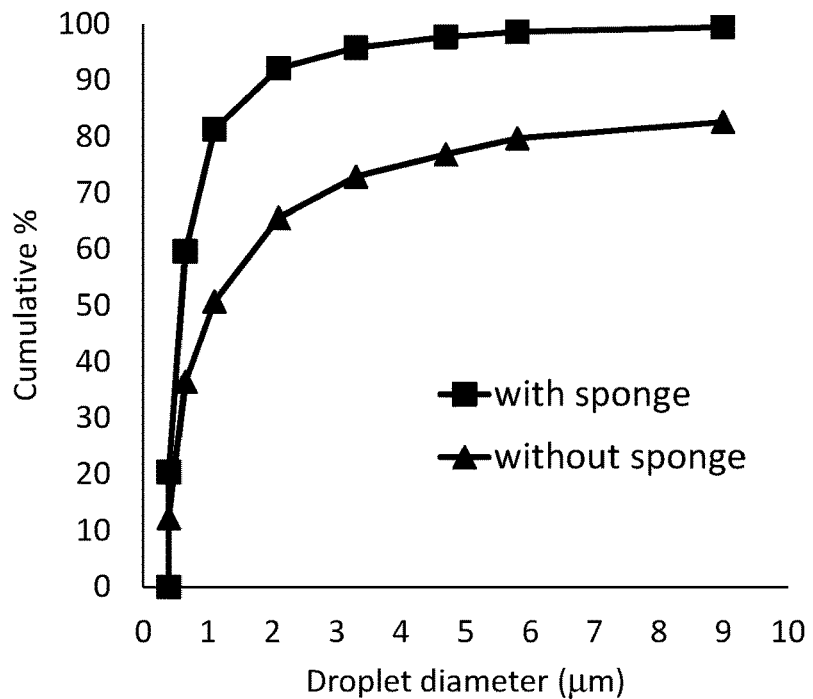
FIG. 6 shows a cumulative droplet size distribution of an aerosolized aqueous solution of a water soluble dye produced by a nebulizer having (squares), or devoid of (triangles), a liquid absorbing material.

The cumulative droplet size distribution of an aerosolized aqueous solution of a water soluble dye produced using a nebulizer according to some embodiments, in the absence or presence of a sponge was tested. The results, presented in FIG. 6 (square—with a sponge; triangle—without a sponge) indicate that in the presence of a liquid absorbing material about 100% of the droplets have diameters of less than 5 microns, wherein 80% of the droplets have diameter of less than 1 micron. However, in the absence of a liquid absorbing material, only about 70% of the droplets have a diameter of less than 5 microns.

Example 2—Measurements of Viscous Water Aerosol Droplet Diameter

Figure 7:
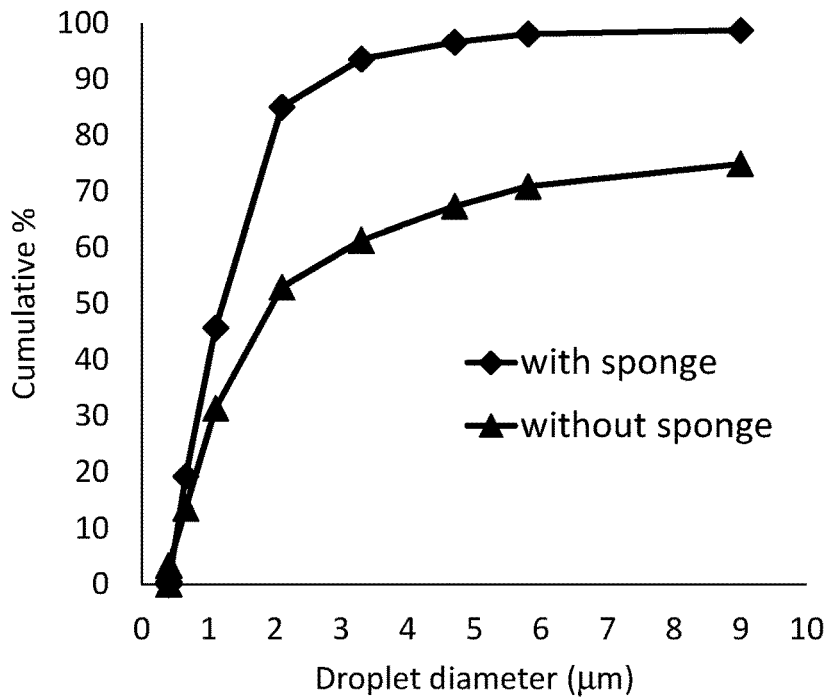
FIG. 7 shows a cumulative droplet size distribution of an aerosolized aqueous solution of a water soluble dye containing glycerol (5%) produced by a nebulizer having (diamonds), or devoid of (triangles), a liquid absorbing material.

The cumulative droplet size distribution of an aerosolized aqueous solution of a water soluble dye containing glycerol (5%) produced using a nebulizer according to some embodiments, in the absence or presence of a sponge was tested. The results, presented in FIG. 7 (square—with a sponge; triangle—without a sponge) indicate that in the presence of a liquid absorbing material about 95% of the droplets have a diameter of less than 5 microns, wherein 85% of the droplets have a diameter of less than about 2 micron. However, in the absence of a liquid absorbing material, only about than 60% of the droplets have a diameter of less than 5 microns.

Figure 8:
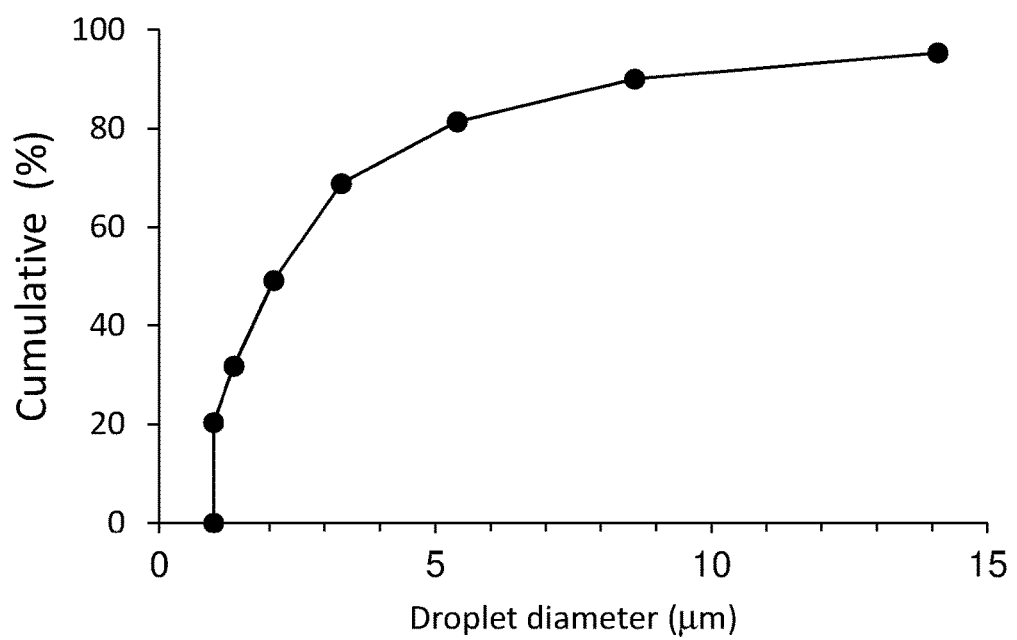
FIG. 8 shows cumulative droplet size distribution of commercial Ventolin® (5 mg/ml albuterol) aerosol produced by a nebulizer having a liquid absorbing material.

Example 3—Measurements of Aerosol Droplet Diameter of a Pharmaceutical Composition The cumulative droplet size distribution of commercial Ventolin® (5 mg/ml albuterol) aerosol produced using a nebulizer according to some embodiments, in the presence of a sponge was tested. The results, presented in FIG. 8 indicate that about 90% of the droplets have a diameter of less than 9 microns, wherein 80% of the droplets have a diameter less than 5 microns.

Figure 14:
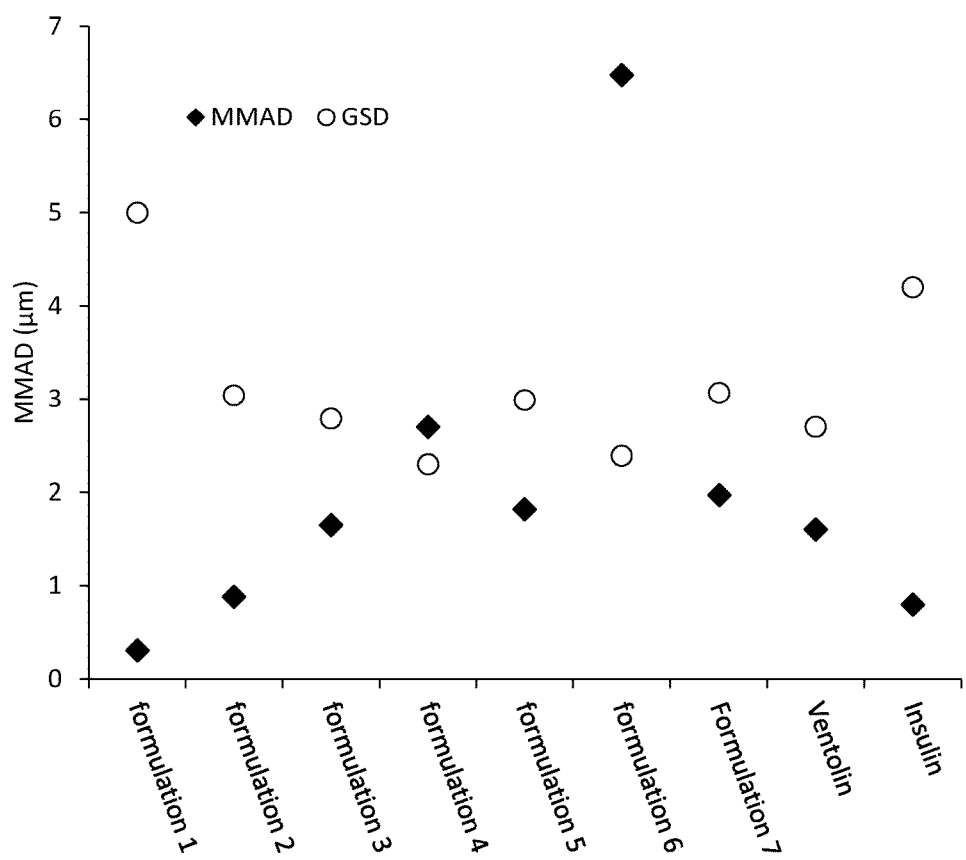
FIG. 14 represents the MMAD (diamond) and GSD (circle) values for various aqueous formulations containing a soluble dye tracer.

Example 4—Measurements of Aerosol Droplet Diameter Produced by a Nebulizer Having a Wetting Mechanism and a Liquid Absorbing Material The cumulative droplet size distributions for different aqueous formulations of a water soluble dye (Formulations 1-7), Ventolin™ and insulin was measured (FIG. 14)—Droplet size distributions were obtained using a cooled next generation impactor (NGI) operated at a flow rate of 15 liters/min. The results indicate that the values of mass median aerodynamic diameter (MMAD) and Geometric Standard Diameter (GSD) vary within the range of about 0.4-7 µm and about 2-5 (two to five) µm, respectively.

Figure 15:
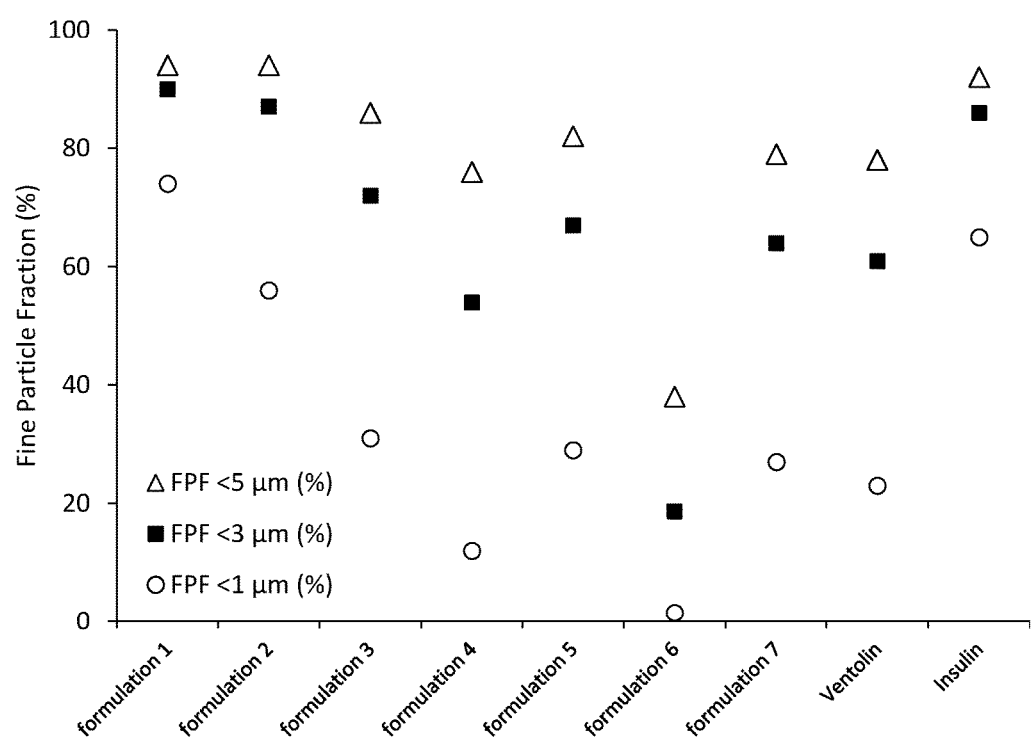
FIG. 15 represents fine particle fractions (FPF) of the aqueous formulations shown in FIG. 14.

The fine (below 5 µm) and extra fine (below 3 µm) particle fractions obtained for the different formulations are presented in FIG. 15.

Example 5—Analysis of Aerosol Droplet Diameter

Figure 16:
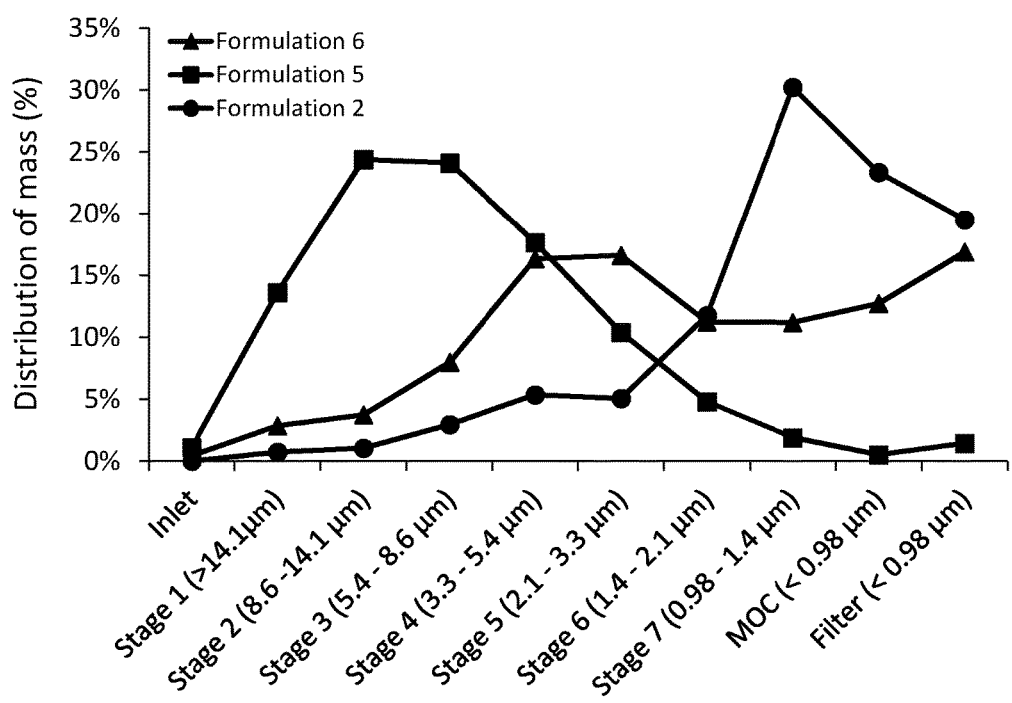
FIG. 16 represents the mass distribution on Next generation impactor (NGI; an analytical instrument that measures droplet size distribution) plates for formulations 2 (circle), 5 (square) and 6 (triangle)

Distribution of mass on Next generation impactor (NGI) plates for various aqueous formulations (2, 5 and 6) containing a soluble dye tracer having different physiochemical properties is presented in FIG. 16. Formulations 2, 5 and 6 were selected for the following reasons: formulation 2 provides very small droplets suitable for systemic delivery, formulation 6 gives droplets at a size suitable for delivery to the central airways, and formulation 5 gives large droplets suitable for nasal delivery. The results highlight the advantage of the nebulizers disclosed herein: the aerosols obtained using the nebulizers may be used for targeting pharmaceutical compositions to various areas of the respiratory system.

An additional important aspect presented in FIG. 16 is the modality of the size distribution. By designing the formulation with proper liquid spreading, the modality may be controlled. For example, using an appropriate formulation, the modality may be changed from uni-modal to bi-modal and even tri-modal.

Example 6—Analysis of Aerosol Droplet Delivery

Figure 17:
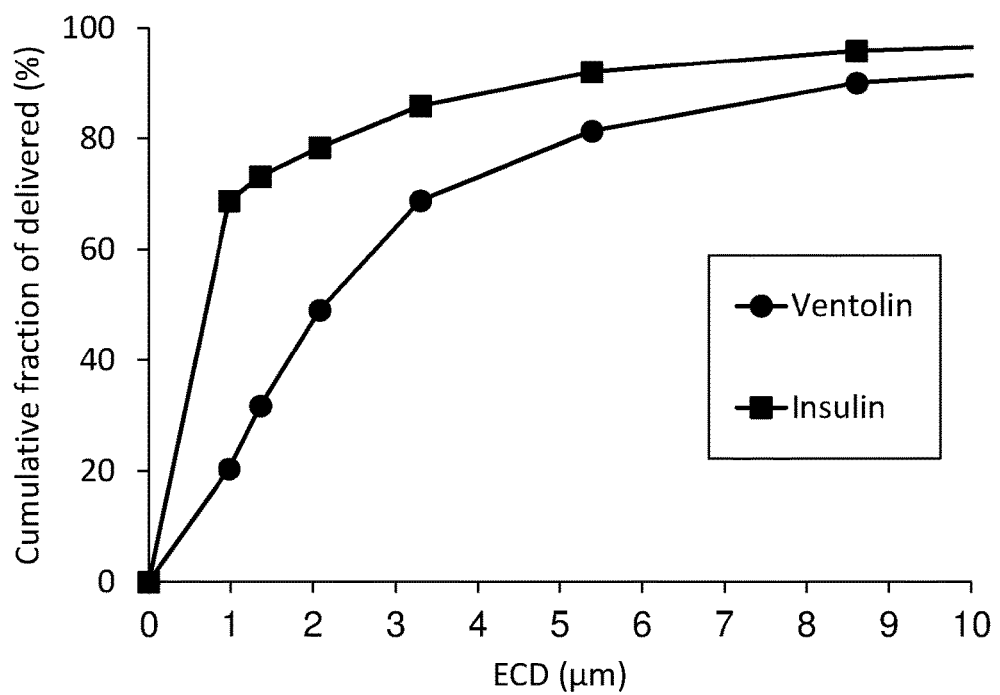
FIG. 17 represents cumulative size distribution plots of Ventolin™ (circle) or insulin (square), produced using a nebulizer having a rotatable wetting mechanism, as a function of effective cut-off diameters (ECD).

Cumulative size distribution plots, for formulations of Ventolin™ and insulin, was measured using NGI (FIG. 17). As shown in the figure, the MMAD obtained for Ventolin™ is around 2.5 microns, which is conducive for the delivery of bronchodilators to the central airways. On the other hand, the MMAD for insulin is lower than 1 micron, which is conducive for delivery into the deep lung and hence for systemic uptake.

The invention claimed is:

1. A nebulizer comprising a porous medium configured to produce aerosols, a displaceable wetting mechanism configured to spread a liquid over the porous medium thereby to wet the porous medium and a gas channel configured to introduce pressure gradient to the porous medium, wherein the displaceable wetting mechanism comprises a rotatable elongated member configured to move across the surface of the porous medium, thereby to homogeneously or semi-homogeneously spread the liquid over the surface.

2. The nebulizer of claim 1, wherein the rotatable elongated member is movable to cover approximately all the surface of the porous medium.

3. The nebulizer of claim 1, wherein the displaceable wetting mechanism further comprises an actuator configured to displace or induce the displacement of the rotatable elongated member.

4. The nebulizer of claim 3, wherein the rotatable elongated member comprises a first magnet, and the actuator comprises a second magnet, magnetically associated with said first magnet, such that by moving the second magnet displacement of the rotatable elongated member is induced.

5. The nebulizer of claim 4, wherein said first and/or second magnet comprise a plurality of magnets.

6. The nebulizer of claim 5, wherein one or more of the plurality of magnets comprises an electromagnet.

7. The nebulizer of claim 3, wherein the actuator comprises a motor configured to displace the rotatable elongated member.

8. The nebulizer of claim 1, wherein the rotatable elongated member is at least partially coated with polytetrafluoroethylene.

9. The nebulizer of claim 1, wherein the porous medium comprises a plurality of pores and wherein the rotatable elongated member is configured to force at least portions of the liquid into at least some of the plurality of pores of said porous medium.

10. The nebulizer of claim 1, further comprising an opening configured to deliver the aerosols to a respiratory system of a subject.

11. A nebulizer cartridge comprising a porous medium and a displaceable wetting mechanism configured to spread a liquid over the porous medium thereby to wet the porous medium, wherein the displaceable wetting mechanism comprises a rotatable elongated member.

12. The nebulizer cartridge of claim 11, wherein the porous medium comprises a plurality of pores, and wherein at least some of said plurality of pores comprise liquid.

13. The nebulizer cartridge of claim 12, wherein said liquid comprises a pharmaceutical composition.

14. The nebulizer cartridge of claim 11, wherein the rotatable elongated member further comprises an actuator configured to displace or induce the displacement of the rotatable elongated member.

15. The nebulizer cartridge of claim 14, wherein the rotatable elongated member comprises a first magnet, and the actuator comprises a second magnet, magnetically associated with said first magnet, such that by moving the second magnet displacement of the rotatable elongated member is induced.

16. The nebulizer cartridge of claim 11, configured to be inserted to a nebulizer main body.

17. The nebulizer cartridge of claim 16, wherein the nebulizer main body comprises an opening configured to deliver aerosols.

18. A nebulizer system comprising
a housing;
an opening in the housing configured to deliver aerosols to a subject;
the cartridge of claim 11;
a receptacle configured to receive the cartridge; and
a gas channel.

19. The nebulizer system according to claim 18, wherein the rotatable elongated member comprises an actuator configured to displace or induce the displacement of the rotatable elongated member.

20. The nebulizer system according to claim 19, wherein the actuator comprises a shaft, configured to be mechanically connected to the wetting mechanism.

* * * * *